(12) United States Patent
Goldstein et al.

(10) Patent No.: US 11,998,352 B2
(45) Date of Patent: Jun. 4, 2024

(54) METHOD AND DEVICE FOR NEUROLOGICAL SCREENING

(71) Applicant: REBIScan, Inc., Boston, MA (US)

(72) Inventors: Lee Goldstein, Newton, MA (US); Justin Shaka, Boston, MA (US); Robert Winsor, Hamilton, VA (US); James Esser, Ashburn, VA (US); Shane Pixton, Broad Run, VA (US)

(73) Assignee: REBIScan, Inc., Boston, MA (US)

( * ) Notice: Subject to any disclaimer, the term of this patent is extended or adjusted under 35 U.S.C. 154(b) by 486 days.

(21) Appl. No.: 17/131,495

(22) Filed: Dec. 22, 2020

(65) Prior Publication Data
US 2021/0219911 A1 Jul. 22, 2021

Related U.S. Application Data

(60) Provisional application No. 62/954,878, filed on Dec. 30, 2019.

(51) Int. Cl.
*A61B 5/00* (2006.01)

(52) U.S. Cl.
CPC .......... *A61B 5/4884* (2013.01); *A61B 5/0059* (2013.01); *A61B 5/4064* (2013.01); *A61B 5/742* (2013.01); *A61B 2560/02* (2013.01)

(58) Field of Classification Search
CPC ... A61B 5/4064; A61B 3/0008; A61B 3/0041; A61B 3/0091; A61B 5/163; A61B 5/4884; A61B 5/162; A61B 5/0059; A61B 5/742; A61B 2560/02; A61B 3/113; A61B 3/12; A61B 5/7425
See application file for complete search history.

(56) References Cited

U.S. PATENT DOCUMENTS

| | | | |
|---|---|---|---|
| 2006/0025658 A1* | 2/2006 | Newman | A61B 3/12 600/301 |
| 2016/0213301 A1* | 7/2016 | Port | A61B 5/743 |
| 2017/0135577 A1* | 5/2017 | Komogortsev | A61B 5/168 |

* cited by examiner

*Primary Examiner* — Matthew Kremer
*Assistant Examiner* — Elina Sohyun Ahn
(74) *Attorney, Agent, or Firm* — Amardeep S. Grewal; Reed Smith LLP

(57) ABSTRACT

A neurological screening device and method for assessing brain dysfunction of a subject including a projection apparatus configured to project an image onto retinas of a subject, detectors configured to capture light reflected from the retinas, the reflected light indicating a fixation of the eyes, a controller configured to generate baseline cognitive performance data based at least in part on a presence or absence of fixation, cause output of a plurality of assessment images on displays of the neurological screening device, the plurality of assessment images corresponding to a cognitive assessment configured to stress the frontal lobe of the subject, generate stressed cognitive performance data based at least in part on a presence or absence of fixation during the cognitive assessment, and determine brain dysfunction of the subject based at least in part on the baseline cognitive performance data and the stressed cognitive performance data.

42 Claims, 18 Drawing Sheets

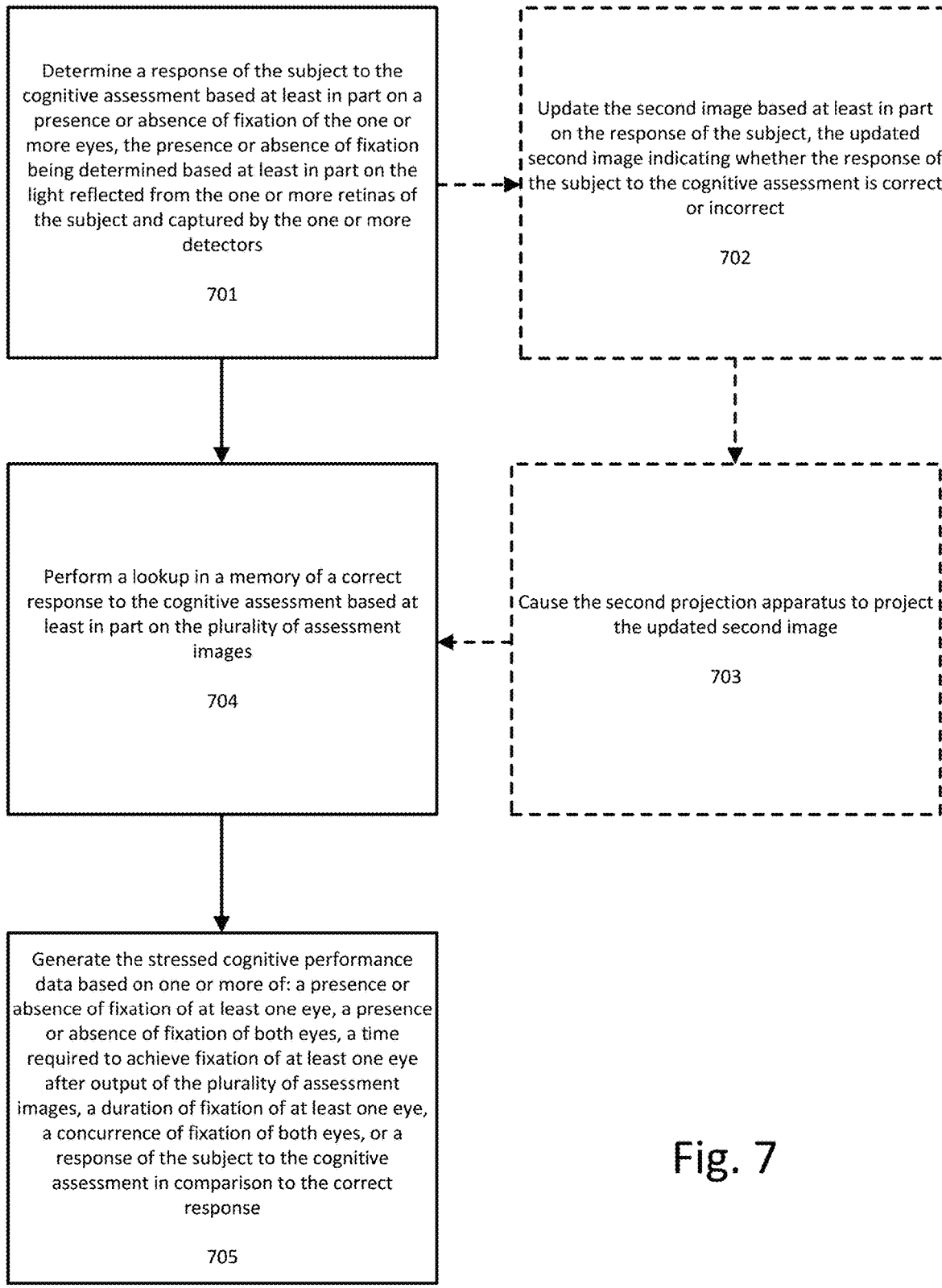

METHOD AND DEVICE FOR NEUROLOGICAL SCREENING

RELATED APPLICATION DATA

This application claims priority to U.S. Provisional Application No. 62/954,878, filed Dec. 30, 2019, the disclosure of which is hereby incorporated by reference in its entirety.

BACKGROUND

Brain dysfunction, including injury and consequences related to concussive and subconcussive traumatic brain injury ("TBI"), either single or repeated incidents, can be difficult to diagnose, prognose, and monitor. Moreover, the histories and circumstances of such injuries are often incomplete, and additionally, the clinical signs and symptoms are difficult to assess, often nonspecific, and frequently overlap with a broad range of common neuropsychiatric disorders. Although most patients with neurological dysfunction resulting from mild forms of TBI (mTBI) make a full recovery, a significant subset does not. Incomplete or complicated recovery is more frequent in individuals who have sustained repetitive head injuries (RHI). Individuals with RHI are also at increased risk of persistent post-traumatic symptoms, such as executive dysfunction attributable to the frontal lobes, and long-term complications, including serious neurological sequelae such as chronic traumatic encephalopathy (CTE). Simple interventions, such as removing the patient from risky environments, may prevent or reduce the risk or severity of these complications by allowing time for the brain to heal and preventing further injury. However, intervention requires prompt and accurate identification and monitoring of patients who are at increased risk for adverse outcomes following these common injuries.

Frequently, the identification of brain dysfunction resulting from brain injury does not take place until long after the injury has occurred, resulting in additional risk of further injury and complications. This is because the diagnosis and treatment of such dysfunction typically requires a lengthy clinical assessment of the subject and examination of their frontal lobe functioning, and such assessments are not readily available on-site or within high-risk environments.

Accordingly, there is a need for improvements in neurological assessment devices and methods of neurological assessment that allow for rapid, non-invasive, and objective evaluation of brain dysfunction.

BRIEF DESCRIPTION OF DRAWINGS

FIG. 7 illustrates a flowchart for generating stressed cognitive performance data corresponding to a cognitive performance of a frontal lobe of a subject while stressed according to an exemplary embodiment.

DETAILED DESCRIPTION

Figure 1A:
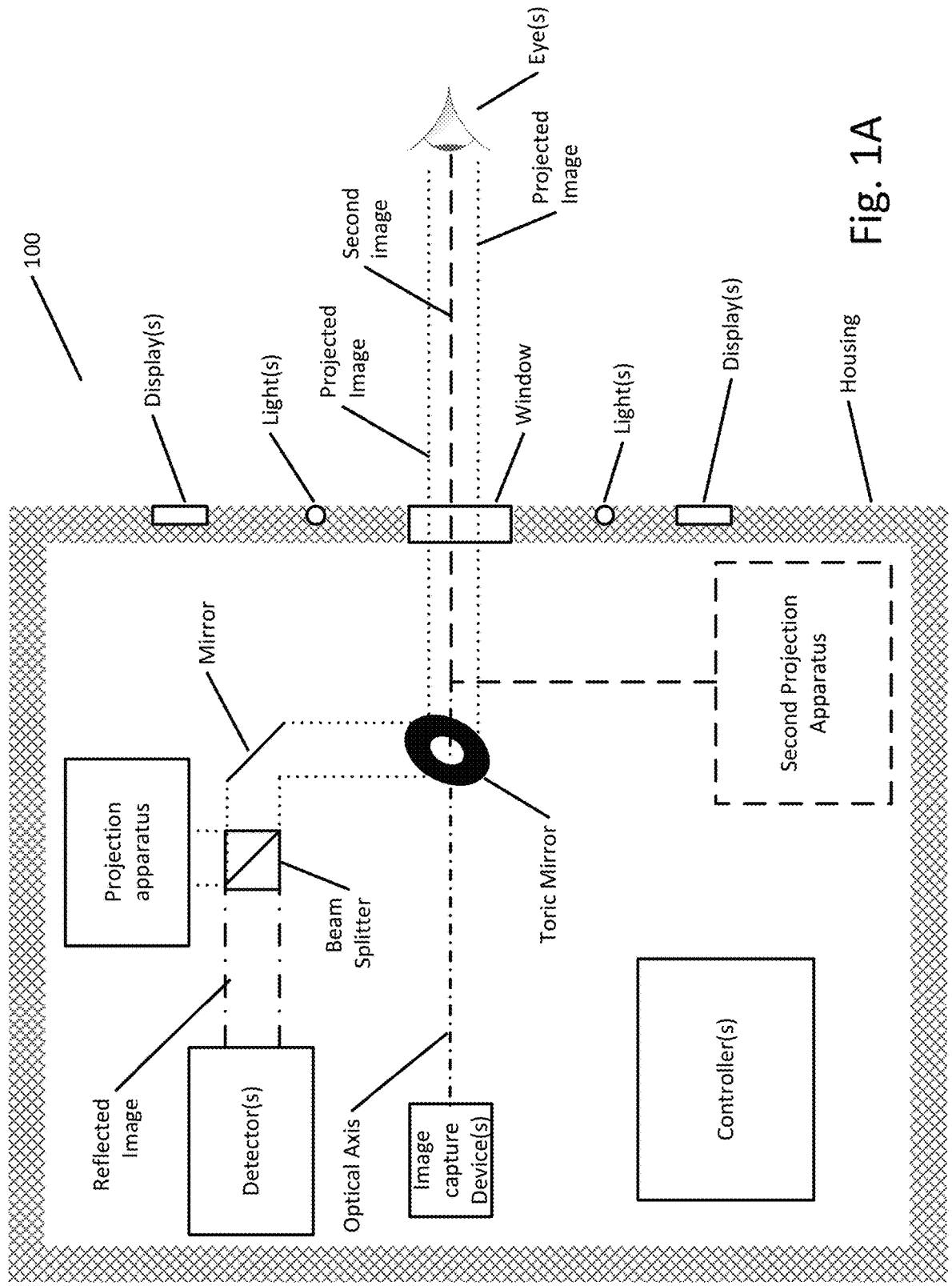
FIGS. 1A-1B illustrate the components and modes of operation of neurological screening devices according to exemplary embodiments.

It is to be understood that at least some of the figures and descriptions of the invention have been simplified to illustrate elements that are relevant for a clear understanding of the invention, while eliminating, for purposes of clarity, other elements that those of ordinary skill in the art will appreciate also comprise a portion of the invention. However, because such elements do not facilitate a better understanding of the invention, a description of such elements is not provided herein.

Applicant has discovered devices and methods for non-invasive neurological screening of the brain, particularly the frontal lobes of the brain, for the purpose of assessing frontal lobe function or brain dysfunction associated with neuropsychiatric disease, head injury, medical or metabolic disturbance(s), drug-related or toxic exposure(s), or other condition(s) that transiently or permanently impairs central nervous system (CNS) function.

The devices and methods disclosed herein provide a noninvasive tool and objective technique for rapid evaluation and longitudinal monitoring of brain dysfunction, including abnormalities of the frontal lobes. In particular, the disclosed devices and methods utilize retinal scanning, eye fixation measurement, and measurements of additional oculomotor functions, to assess visual impairments that are indicative of brain injury or trauma.

There are clear links between frontal lobe injury and abnormal performance on oculomotor function metrics. Control of eye movement and vision depends on the integrity and coordination of key brain areas, including the frontal, parietal, and supplementary eye fields (FEF, PEF, SEF). Saccades are initiated via superior colliculus (SC) and brainstem gaze centers (BCH) and inhibited by the midbrain substantia nigra pars reticulata (SNR). Antisaccades, reflexive saccades, and saccadic planning are modulated by dorsolateral prefrontal cortex (DLPC), an important subregion in the frontal lobe. Binocular motor fusion control resides in the pineal, midbrain, and cerebellar areas. Multimodal association areas in the frontal lobes of the human brain are also critically involved in cognitive processing, sensorimotor coordination, affect and behavior regulation, executive function, and consciousness; conversely, the frontal lobes are exquisitely sensitive to dysfunction resulting from stress, disease, or trauma.

The disclosed devices and methods leverage the relationship between oculomotor function and brain dysfunction and provide improved frontal lobe assessment by stressing frontal lobe function (by incorporating specific cognitive tasks that critically depend on frontal lobe functional integrity and network integration) while simultaneously measuring oculomotor function, including fixation of each eye individually, binocularity of the eyes, misalignment between the two eyes (i.e., microstrabismus), saccadic eye movement and latency, and eye convergence.

Stressing the frontal lobe while measuring these metrics significantly increases the accuracy and specificity of a cognitive assessment, thereby enabling a rapid, highly accurate probe of ocular dysfunction, and thereby frontal lobe and brain dysfunction, in patients who have suffered brain injury.

FIG. 1A illustrates a neurological screening device 100 according to an exemplary embodiment. As shown in FIG. 1A, the device 100 includes a projection apparatus configured to project an image onto one or more retinas of one or more eyes of a subject. The projection apparatus is positioned within a housing and configured to project the projected image (shown with dotted lines) through a window of the housing and onto one or more retinas of one or more eyes of a subject. The light from the projected image enters the eyes, is imaged onto the retinas, and is then reflected off the retinas.

The projected image and the projection apparatus can take a variety of different forms. The projection apparatus can be a scan based projector with moving parts that scans the retina or a stationary projection apparatus with no moving parts that projects an image onto the retina. The projected image can be a predefined or stored image that is projected by the projection apparatus, an image that is created by components of the projection apparatus, or a stimulus that is scanned by the projection apparatus to create the appearance of a projected image to a subject. Implementations of the projection apparatus and projected image are described in greater detail below.

The projected image can be a ring image that is generated by a projection apparatus that includes a light source configured to project light and a concave toroidal mirror configured to reflect the light projected from the light source into the ring image. In this example of a stationary projection apparatus, there are no moving parts and the projected image is created from the reflection of the light from the concave toroidal mirror (which will focus the light into a ring).

The ring image can also be generated by a projection apparatus that includes a light source configured to project a laser beam of light through an axicon lens to generate a circular light projection and a toroidal lens configured to focus the circular light projection into the ring image.

Additionally, the ring image (or the appearance of a ring image) can also be generated by a laser beam scanning projection apparatus that includes a light source configured to project light onto a first concave mirror that is configured to rotate about a rotation axis and re-image the light projected from the light source onto a second concave mirror. Although at any given moment only a single beam of light is hitting the second concave mirror (and then the eye of the subject), the rotation by the first concave mirror occurs at high enough speeds to create the appearance of the ring image on the second concave mirror. The use of spinning mirror to generate a ring image is discussed further in U.S. Pat. No. 7,959,292 (issued Jun. 14, 2011), titled "Vision Screener," the disclosure of which is hereby incorporated by reference in its entirety. As discussed in greater detail below, the projection apparatus can also be implemented using alternative techniques and components for projecting a projected image.

The projection apparatus can also be an image projector configured to project a stimulus, such as a grid of double lines or a plurality of concentric circles. In this case, fixation can be assessed using distortions in the reflected image caused by wave-front error when the light is reflected through the structures of the eye and then detected by photodetectors.

As discussed above and as used herein, the term "projection apparatus" includes multiple different types of systems for determining fixation, including image projection systems that project an image onto the retina, laser scanning systems that project/scan a laser beam across the retina, and/or other systems used to assess fixation.

The device 100 additionally includes one or more detectors disposed conjugate to the one or more retinas. As used herein, the term "conjugate" refers to conjugate points of a lens system, meaning that the photodetectors are disposed at the image point corresponding to the object point of the retinas such that the retinas of the subject are imaged onto the photodetectors.

The one or more detectors are configured to capture a reflected image reflected from the one or more retinas in response to the projected image. As discussed in greater detail further below, the reflected image includes information indicating fixation of the one or more eyes. The detectors can be any suitable type of optical sensing detectors. For example, the detectors can be charge coupled device (CCD) sensors, complementary metal-oxide-semiconductor (CMOS) sensors, etc.

The reflected image can then be converted by the detectors (or a controller controlling these components) into reflected light data. The reflected light data include information indicating a fixation of the eye(s) of the subject. Fixation can be calculated, for example, based on one or more polarization-related changes between light emitted by the light source and light received from the one or more eyes of the patient, as described in U.S. patent application Ser. No. 14/806,593 (filed Jul. 22, 2015), titled "METHOD AND APPARATUS FOR FIXATION MEASUREMENT," the disclosure of which is hereby incorporated by reference in its entirety.

Fixation can additionally be determined based on polarization based changes in an image and a reflected image, as described in U.S. patent application Ser. No. 14/978,865 (filed Dec. 22, 2015), titled "APPARATUS AND METHOD FOR FIXATION MEASUREMENT WITH REFRACTION ERROR MEASUREMENT USING IMAGE SENSING DEVICES," the disclosure of which is hereby incorporated by reference in its entirety.

For example, when the image is a ring image, fixation of one or more eyes can be calculated based at least in part on one or more polarization-related changes between attributes of the scanning ring image and the reflected ring image. The ring in the reflected image can provide one of two general types of characteristics which are used to determine fixation.

For the first type, the ring image has two shorter arc regions that are dimmer than average, and two that are brighter than average. The two bright regions are roughly 180 degrees apart from each other, as are the two dim regions, with dim regions separating bright regions. This image would indicate a successful measurement of fixation. A minimum of two sequential image captures that are successful measurements of fixation can indicate the person has successfully demonstrated ability to fixate in that eye.

For the second type, a ring in the reflected image has a larger arc-length region that is bright, and there is only one such section. The ring likewise has one larger arc-length region that is dim, and there is only one. This image constitutes a failure to fixate, and indicates that scanning for fixation needs to continue.

Fixation can also be determined by measuring distortion of the image due to wave-front error, as described in U.S. Pat. No. 9,675,248 (issued on Jun. 13, 2017), titled "METHOD AND APPARATUS FOR FIXATION MEASUREMENT AND REFRACTION ERROR MEASUREMENT USING WAVE-FRONT ERROR," the disclosure of which is hereby incorporated by reference in its entirety. In this case, the image can be projected by an image projector and can include, for example, a circle or a grid in addition to the fixation target. Distortions in the reflected image can be compared with the projected image to identify fixation.

The device 100 can optionally include a second projection apparatus positioned within the housing and configured to project a second image that is configured to appear to the subject to be centered within the projected image. The second image can be, for example, a fixation target. The fixation target can be utilized during a baseline assessment or cognitive assessment to provide a visual target for a subject. For example, a subject can be directed to focus on the fixation target. As will be discussed in greater detail below, the second image can also be an image configured to inform the subject whether they have responded correctly or incorrectly to a cognitive assessment or stage of a cognitive assessment. For example, the second projection apparatus can project a check mark image when a subject correctly responds to a particular cognitive assessment and can project an "x" mark image when a subject responds incorrectly.

Although the second image appears to the eye(s) of subject to be centered within the projected image, the second projection apparatus does not necessarily have to be positioned along the optical axis of the eye. As is explained in more detail below, the apparatus can be configured such that second projection apparatus is not positioned along the optical axis of the eye but still projects a second image that appears to lie on the optical axis to the eyes of a subject. The second projection apparatus can include, for example, a display configured to generate the second image and a reflector configured to reflect the fixation target onto a window of the housing that surrounds the projection apparatus, the one or more detectors, and the second projection apparatus.

As shown in FIG. 1A, the neurological screen device 100 can additionally include image capture device(s) disposed conjugate to one or more corneas of the one or more eyes of the patient and configured to capture a diagnostic image including one or more pupils of the one or more eyes when the one or more pupils are illuminated by retroreflected light from the one or more retinas in response to the projected image. This process is described in more detail below.

Light from the projection apparatus enters the eye and is focused onto the retina. There is a reflected component of this light that is captured by the photodetectors and that is used to assess fixation. This type of reflection is referred to as "specular reflection." However, there is an additional type of reflection, referred to as "diffuse reflection," that causes illumination of tissue near the retina due to light scattering from the retina. This diffuse reflection of the projected light illuminates the cornea and allows for the capture of the corneal image by the image capture device.

While the pupil and the cornea are technically distinct components of the eye, the cornea resides within the eye just in front of the pupil, so that an image capture device that is disposed conjugate to (focused on) the cornea will essentially also be disposed conjugate to (focused on) the pupil. In terms of the anatomy of the eye, the cornea is the outermost layer of the eye. The pupil is created by the iris of the eye, and sits just a millimeter or two behind the cornea—there is a small gap of fluid between the two. The fluid gives the optical appearance as if the pupil is even closer to the cornea than it actually is.

Therefore, with respect to image capture devices that view the cornea or pupil from a distance of at least ⅓ meter, the terms cornea and pupil can be used interchangeably with respect to the focus area of the image capture device. In other words, if the image capture device is focused on the cornea, it is also focused on the pupil.

The image capture device can be any type of suitable digital image capture device, that uses, for example, charge-coupled device (CCD) or complementary metal-oxide-semiconductor (CMOS) technology, and can include, for example, a lens, an electronic shutter, a fixed iris, a focal plane array sensor, etc. The image capture device can have a lens on it with a focal length chosen such that both pupils can be viewed on the sensor simultaneously, while being set with fixed focus to image the pupils with best resolution. For example, two pupils spaced 75 mm apart while the image capture device is placed 400 mm from the eyes, and using a 5 mm wide sensor would require a lens with a focal length no longer than 25 mm. In practice, since patients may move around a bit during examination, a shorter focal length lens can be chosen to permit easier capture of both pupils. The image capture device can have sufficient resolution (number of pixels spanning the sensor), to get measurements of the pupil sizes of the subject with accuracy exceeding 0.1 mm. For example, a 5 megapixel digital camera with 2 um pixels and a 16 mm lens can be utilized as the image capture device and is able to achieve spatial mapping of the pupils down to 0.05 mm. The image capture device can include any combination of sensor(s) and lens(es) that effect a means of recording a facsimile of conjugate stimuli—in this case, an image of the cornea that is disposed conjugate to the image capture device.

As shown in FIG. 1A, the image capture device is aligned along the optical axis of projected image beam path and is located at the apparent position of the second image (the position where the fixation appears to be located to the subject). In other words, the image capture device is positioned to capture light reflected from the subject's retinas along the same path that the light traveled when entering the eyes. As used herein, the optical axis means the axis of symmetry for the light propagation path of the projected image. For example, if the projected image is a ring image than the axis of symmetry (the optical axis) would lie in the center of the ring image, co-axial with the direction of propagation of the projected image beam path. Note that when the projected image is generated by scanning (such as when using a spinning mirror), the optical axis is still the axis of symmetry of the projected image, and not each individual beam of light that makes up the projected image.

The configuration of the image capture device on the optical axis of the subject's eye and the second projection apparatus off the optical axis of the subject's eye has many technical advantages.

Light from the scanning system illuminates the facial region including one or both eyes. The light can additionally be configured to illuminate only a small area such that the majority of a subject's face other than the subject's eyes is not illuminated. When a spinning mirror is used to generate the projected image, the projected image is referred to as a "scanning image," since the projected image is created by a scanning a beam of light over a circular path. With a scanning image, each eye is able to see the appearance of a ring because the scan mirror is spinning so fast that a subject's eyes perceive it as a circle, rather than a dot being swept in the path of a circle.

The laser light entering the eyes is partially retroreflected back out of the eyes, a portion of which can be captured by a image capture device if the image capture device is sufficiently close (in angle) to the path that the light traveled when entering the eyes. In practice, this angle needs to be less than 5°, and the appearance of brightness of the pupils will increase if the angle is diminished. Therefore, the ideal location for the image capture device is at the apparent center of the circle being swept by the scanning system.

This particular location for the image capture device creates a problem, because it is at a location where a second image, such as a fixation target, would be ideally located. To alleviate this problem, the second projection apparatus that generates the second image is moved to a new location. Since the image capture device is located at the center of fixation, it is ideally placed for viewing both pupils of the test subject (patient under test). Each eye, reflecting a portion of the incoming scanning light, has a pupil that appears very bright (rather than very dark as is normally otherwise the case). Due to the reflectivity of the retina, the returning light is of sufficient brightness to be among the very brightest features in a image capture device image.

In order to align the image capture device with the optical axis and simultaneously allow light retroreflected from the eyes of the subject to reach the image capture device without interfering with the projected image projection path or reflected image path, the neurological screening device 100 of FIG. 1A additionally includes a toric mirror aligned with the optical axis. The toric mirror is configured to reflect the projected image onto the one or more retinas and re-reflect the reflected image onto a propagation path to the one or more photodetectors. To allow light to pass through to the image capture device, the toric mirror includes an aperture configured to allow retroreflected light to pass through to the image capture device.

Figure 1B:
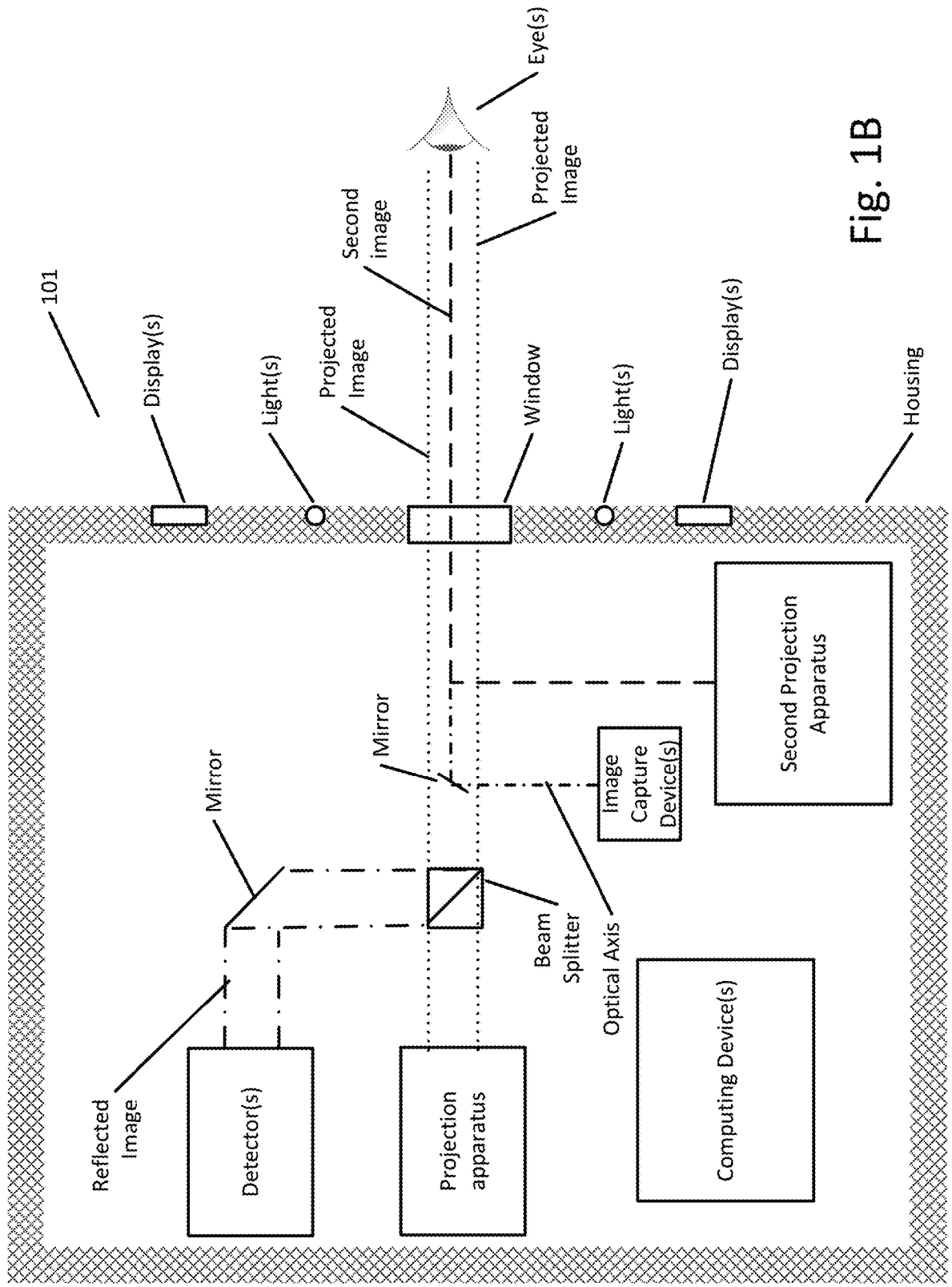

Of course, the neurological screening device can be implemented in alternative ways such that the toric mirror is not required. For example, FIG. 1B illustrates a neurological screening device 101 in which the projecting apparatus generates a ring shape and a mirror is positioned within the ring to reflect retroreflected light towards an image capture device. Since the mirror is small enough to fit within the ring, there is no need for a toric mirror with an aperture. Additionally, if the image capture device is small enough to fit within the projected image being projected, the mirror could be replaced with the actual image capture device itself.

The image capture device can be used to generate and provide metadata during a fixation test. The metadata can be data pertaining to the conditions under which the fixation test is conducted (such as ambient/background light), data pertaining to attributes of the subject's eyes (such as pupil size, location, etc.), or any other information that can be extracted from the images captured by the image capture device. This functionality has many benefits. One benefit is the ability to use the image capture device to measure the amount of background light that exists in the examination room. Ideally, the test for fixation should occur in a dimly-lit setting (or a dark room), such that the pupils of the patient can dilate, which in turn produces a stronger signal for better quality measurement of fixation. If the image capture device detects a background light that is too high, the instrument can alert the user to move the test to a darker location (if possible), or the test can occur but with the metadata attached to the scan record to indicate the test was conducted in higher-than-recommended backlight room conditions. Another benefit of the image capture device is to detect when both pupils are within the regions that are ideal for the scan to occur. A user needs to move the instrument to the correct proximity to the patient (distance from patient, with correct aiming direction) for the scan to detect fixation. Since the image capture device images can be processed in near-real-time to detect whether there are pupils in the correct locations, the image capture device can automatically trigger the start of the test without the user needing to press a button.

Yet another benefit is that since the image capture device system can image the pupils and measure their sizes, it can also add this metadata to the scan data. This data may prove helpful in cases when a patient fails a test for reasons that are not completely due to fixation. For example, if a child is tested immediately after playing outdoors in bright sunlight, the pupils may not have had time to sufficiently dilate to achieve a good signal response. By including the pupil size metadata with the scan, however, this type of reason for failing a fixation test can provide a physician with a reason to re-test rather than necessarily refer the child to a costly specialist. Alternatively, a child may have a partial or full cataract as a reason for failing a fixation test, and the pupil size metadata can further assist a physician in understanding why the child was unable to achieve a good fixation measurement during the scan.

As discussed above, the second projection apparatus is moved to a new location. Although the second projection apparatus is moved to a new location, the second image (such as the fixation target) is kept in the same "apparent" position using a mirror that can be part of the second projection apparatus. It can be located at the same distance from the mirror as the scanning ring (or, the original intended location of the second image). This mirror has a special coating applied to it that allows the infrared light of the scanning system to pass through it with high transmission value, however it reflects a significant portion of visible light from the fixation target projector, for example green light, so it permits the combination of two different sources of light to appear to be placed at the same location despite being physically located in different positions. These mirrors are, to those skilled in the art, commonly referred to as "cold mirrors" because infrared light is historically the "warm" or "hot" part of the spectrum of classical incandescent lamps. Hot mirrors, conversely, reflect the infrared and rather have high transmission of visible light. Either mirror type can be used to combine a visible light source with an infrared light source, and the use of one type of mirror over the other is not a limitation but rather a design choice.

The implementation of a cold mirror, when used in combination with an infrared scanning light for the first projector, permits the infrared scanning light, with its apparent circular shape, to appear to be surrounding the second image, while simultaneously appearing on the same plane as, a fixation target that is produced using visible light (for example, green light on an OLED screen).

An organic light-emitting diode (OLED) screen can be used as the display of the second projection apparatus. The use of an OLED screen fixation target placed in a different location provides an additional benefit. Normally, the OLED screen is a bit large, and can be challenging to locate in such a way that the scan ring can also be viewed. By incorporating the cold mirror (or hot mirror, for alternate method), the OLED can be placed in a location where there is sufficient room for the full size display to be, apparently, superimposed onto the scan ring. The OLED display can then be used to incorporate other attention-grabbing graphics to secure the attention of a young child and draw their fixation into the central target area, thereby assisting the testing process and helping a normal healthy child to pass the test.

The OLED display can be placed near an instrument window of the neurological screening device, located such that it's surface is both centered and 1:1 conjugate to the projected image (such as an apparent ring swept out by the projection apparatus when using a spinning mirror).

As shown in FIGS. 1A-1B, the neurological screening device 100 or 101 additionally includes one or more display(s) disposed on or in an outer wall of the housing. While FIGS. 1A-1B illustrate two displays, any number of displays can be utilized for the purposes of the neurological screening methods disclosed herein. For example, the neurological screening device can have 1 display, 4 displays, or a different number of displays.

The displays are located on a face of the neurological screening device such that they are visible to, and within the field of view of, a subject who is being screened for neurological dysfunction. The displays can lie on the same plane or face of the housing as other output components of the neurological screening devices, including the window by which an image is projected onto the retina(s) of the subject and by which the reflected light returns to the is detector(s) within the housing of the device 100 or 101. As shown in FIGS. 1A-1B, the displays can also lie on the same plane or face of the housing as one or more lights, the function of which is discussed in greater detail below.

The displays of the neurological screening device are utilized to administer and/or assist with implementation of the cognitive assessment that is configured to cognitively stress the subject. For example, the cognitive assessment can be configured to stress the frontal lobe of the subject. The frontal lobe of the subject is stressed by requiring the subject to perform a series of frontal lobe-dependent tasks that have been specifically devised to require ocular responses. The displays can be utilized to present images that are pertinent to the tasks the subject is required to perform. For example, a subject can be instructed to identify matching symbols, shapes, or quantities that appear on one or more of the display screens of the neurological screening device.

The displays can also be used to stress the frontal lobe by presenting interfering stimulus while the cognitive assessment is underway. Both of these techniques can be utilized at the same time. For example, a subject can be required to match shapes shown on two randomly selected display screens out of four display screens while the two other display screens present irrelevant images designed to distract the subject. The use of the display screens as part of the cognitive assessment is described in greater detail with respect to the functionality of controller of the neurological screening device.

As shown in FIGS. 1A-1B, the neurological screening device 100 or 101 can additionally include one or more lights disposed on or in an outer wall of the housing. Similar to the displays, the one or more lights are located on a face of the neurological screening device such that they are visible to, and within the field of view of, a subject who is being screened for neurological dysfunction. The lights can also lie on the same plane or face of the housing as other output components of the neurological screening devices, such as the displays or the window.

As will be discussed in greater detail below, the lights can be used to output a sequence of one or more cues to the subject for the purposes of establishing a baseline cognitive performance of the subject and generating baseline cognitive performance data on the subject. For example, the subject can be directed to fixate on any lights that are activated and then fixate on a fixation target coaxial with the image projected on the retinas of the user. In this case, fixation and time of fixation of the subject can be determined when the subject fixates on the fixation target and a delay between the output of one or more cues, via one or more lights, and detection of fixation can be used to establish a baseline cognitive performance data of the subject, prior to the frontal lobe of the subject being stressed by a cognitive assessment.

The lights can also be activated as part of the cognitive assessment that is configured to cognitively stress the subject, either alone or in conjunction with the displays. Using a combination of lights and images on the displays, the quantity of different types of cognitive assessments (such as particular puzzles the subject must work out or instructions the subject must respond to) numbers in the tens or hundreds of thousands. For example, a subject can be instructed to fixate on the central target every time a light in one of the lights consecutively flashes a quantity of times that is equal to a quantity of items displayed on one of the displays of the neurological assessment device.

Figure 2A:
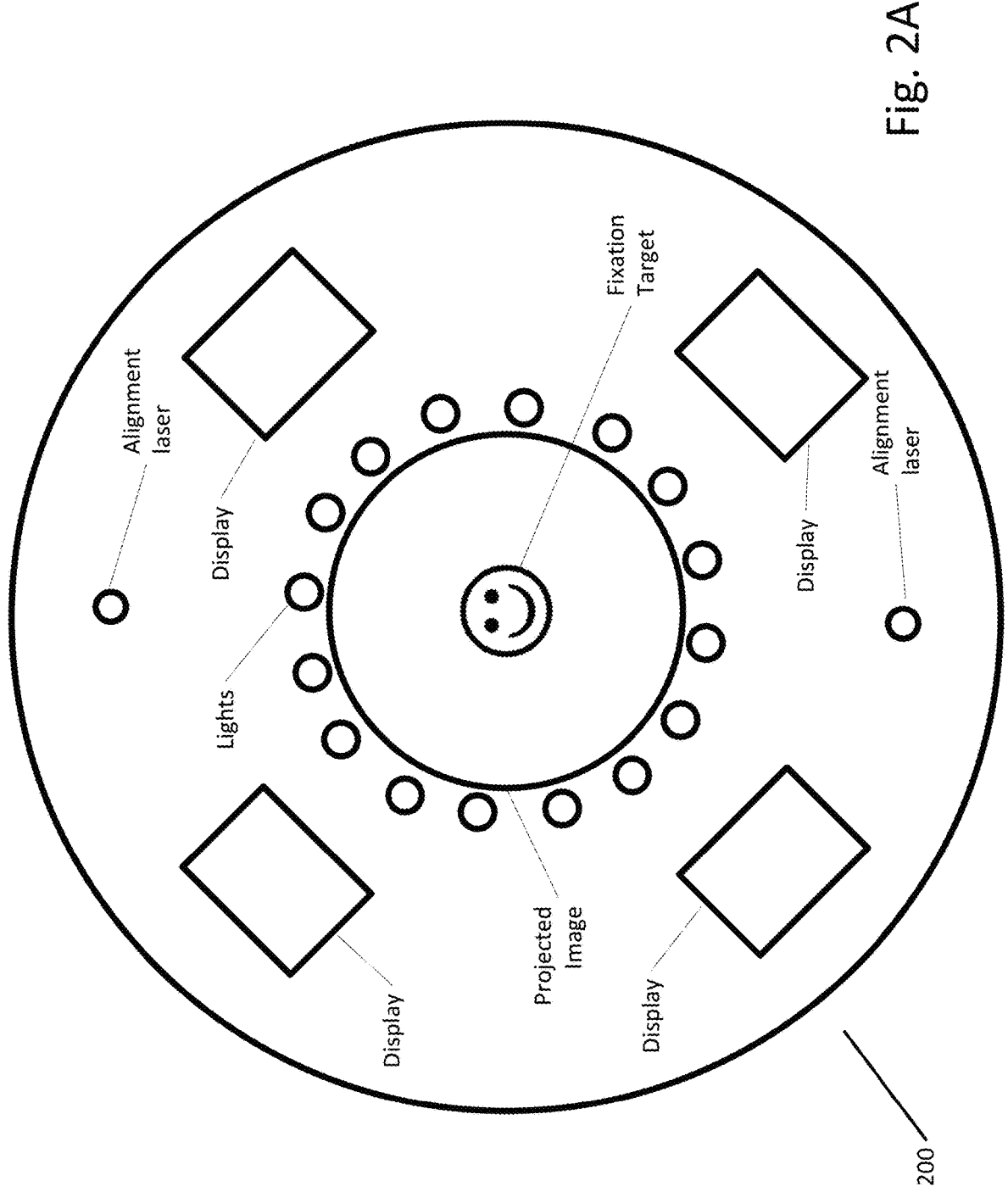
FIGS. 2A-2C illustrate several views of a neurological screening device according to an exemplary embodiment.
Figure 2B:
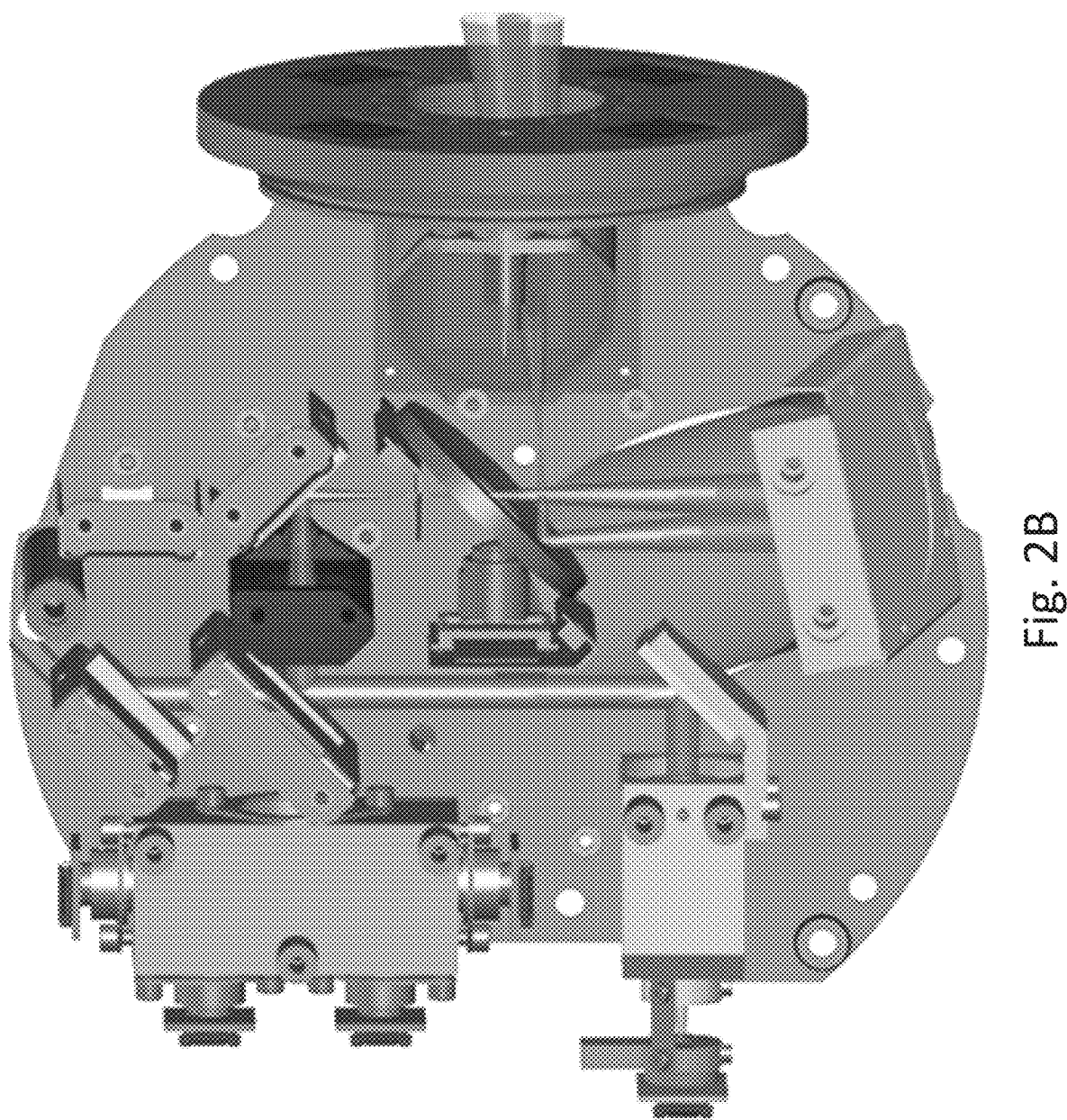
Figure 2C:
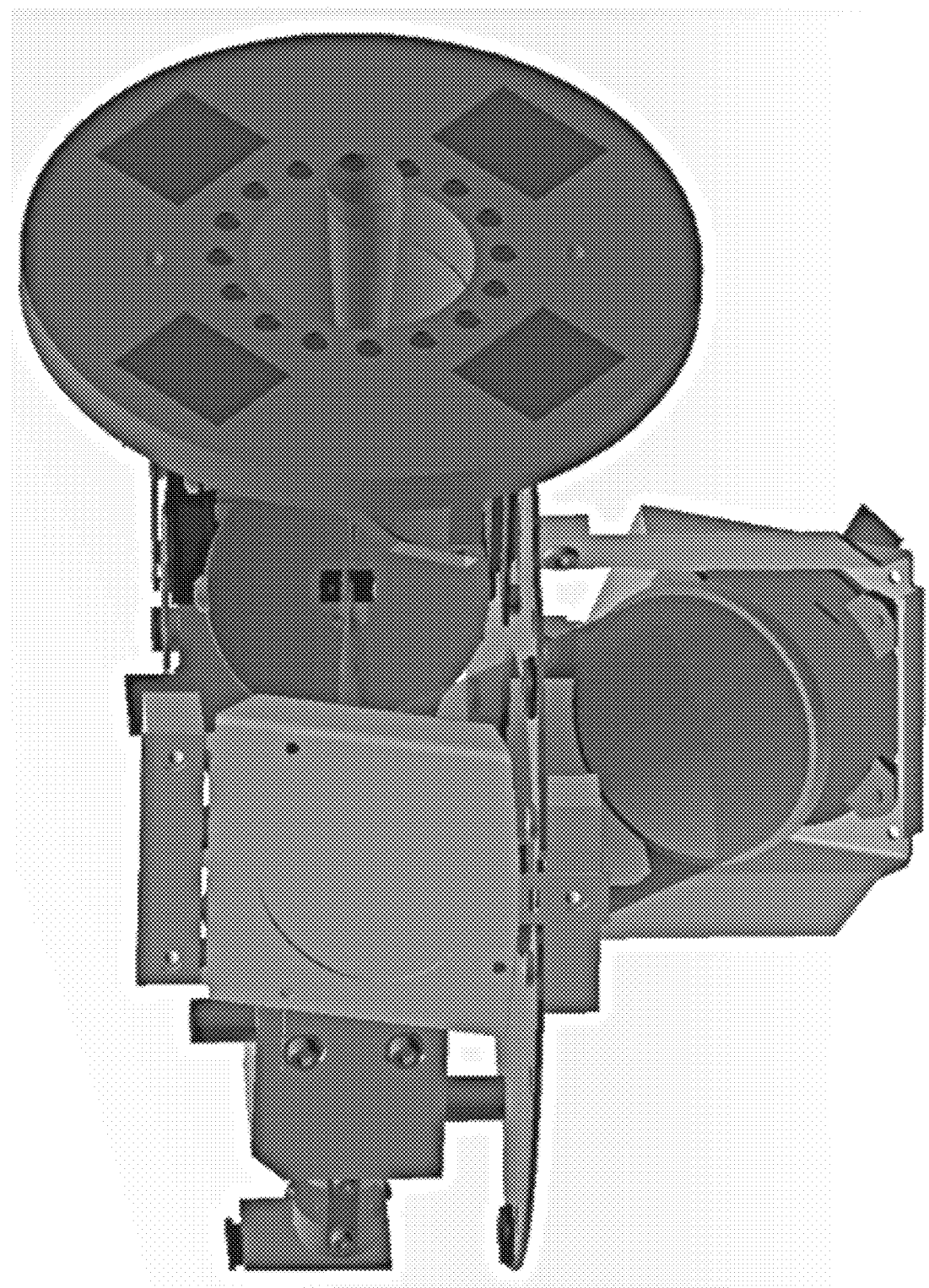

FIGS. 2A-2C illustrate several views of a neurological screening device 200 according to an exemplary embodiment. FIG. 2A illustrates a face of the neurological screening device 200 that includes a central projected ring image (projected by the projection apparatus), a fixation target (projected by the second projection apparatus), sixteen lights, and four displays.

FIG. 2A also illustrates alignment lasers, located above and below the projected image and the fixation target. The alignment lasers can be used as rangefinders and can be, for example, two "micro"-sized laser pointers. Each nominally 650 nm providing a ~2 mm diameter beam, ~350 mm downrange. These can be mounted to the front Bezel of the neurological screening device, one located directly above the window and one directly below, nominally separated 75 mm. These can be internally adjusted such that they point to the center of the patient exit pupil (see section on exit pupil alignment), but with the upper laser oriented slightly right of center while the lower oriented slightly left of center such that at optimal range (400 mm from the apparent focal place of the ring), the two dots are closely spaced side-by-side, separated by 1 mm to 3 mm of distance.

FIGS. 2B-2C illustrate views of the internal and external components of the neurological screening device, including the components previously discussed with respect to FIGS. 1A-1B.

Returning to FIGS. 1A-1B, the neurological screening device 100 or 101 additionally includes a controller. Optionally, multiple controllers can also be utilized. As described in greater in detail with respect to FIG. 13, the controller is a specialized controller having special-purpose components and computer-readable instructions configured to carry out the functionality described herein. The components of the controller include one or more processors, one or more memories, and computer-readable instructions that are stored on the memories and executed by the processors to carry out the functions of the controller.

While not shown in FIG. 1A or 1B (for clarity), the controller is coupled to the other components in the device 100 or 101, including the projection apparatus, the second projection apparatus, the detector(s), the display(s), the light(s), and the image capture device(s). The controller can be coupled via a system interconnection mechanism, such as a system bus.

Figure 3:
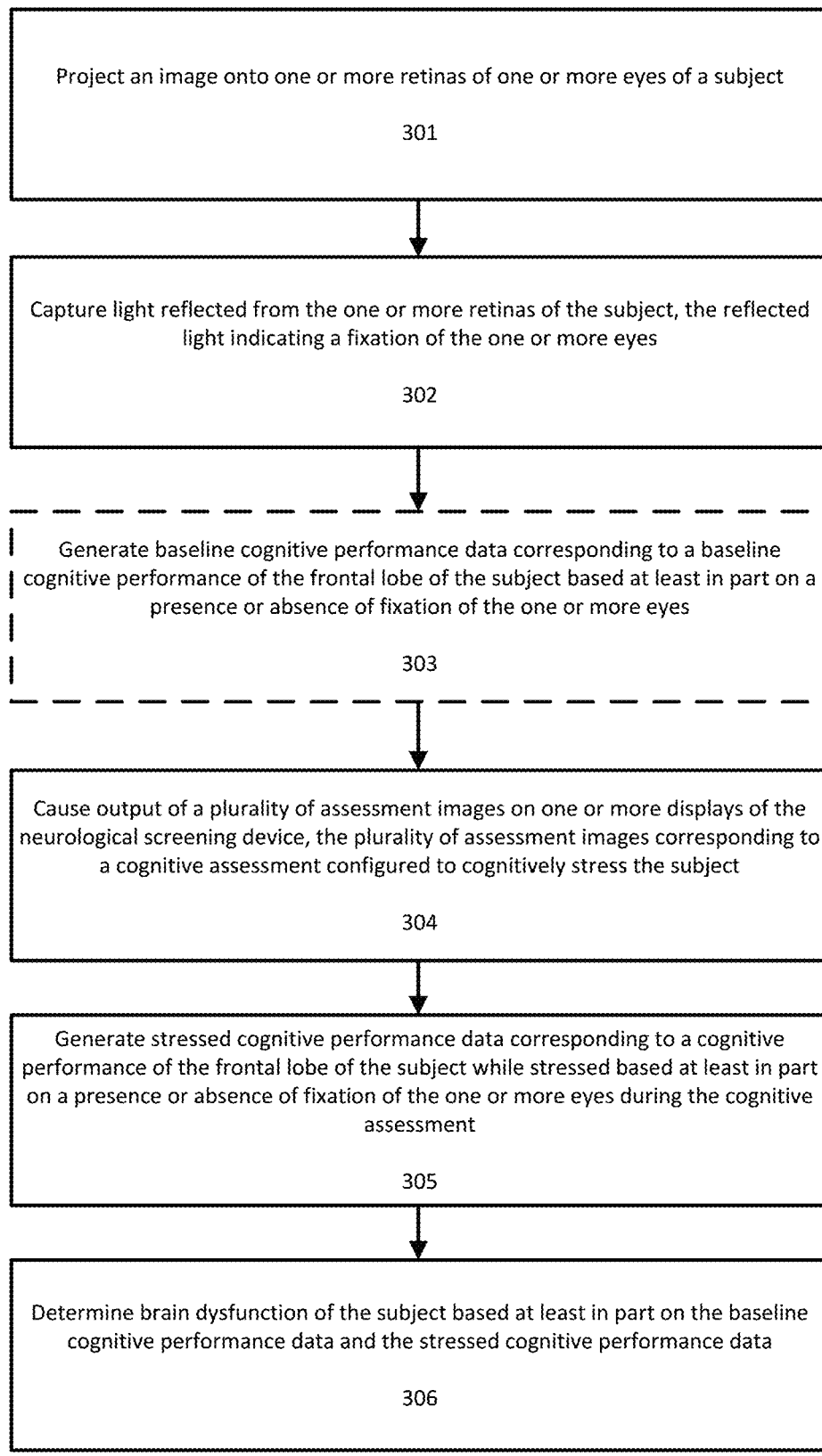
FIG. 3 illustrates a flowchart for performing a neurological screening to assess brain dysfunction according to an exemplary embodiment.

FIG. 3 illustrates a flowchart for performing a neurological screening to assess brain dysfunction according to an exemplary embodiment. At step 301 an image is projected onto one or more retinas or one or more eyes of a subject by the projection apparatus. At step 302 light reflected from the one or more retinas from the subject is captured by the one or more detectors and indicates a fixation of the one or more eyes. Both step 301 and step 302 are discussed in greater detail with respect to FIGS. 1A-1B.

Steps 303-306 are performed by the controller of the neurological screening device. The controller is optionally configured to generate baseline cognitive performance data corresponding to a baseline cognitive performance of the frontal lobe of the subject based at least in part on a presence or absence of fixation of the one or more eyes of the subject (optional step 303). Note that the step of generating baseline cognitive performance data can be omitted, in which case the neurological screening device can determine cognitive dysfunction based solely on stressed cognitive performance data, as discussed below.

The controller configured to cause output of a plurality of assessment images on the display(s) of the neurological screening device, the plurality of assessment images corresponding to a cognitive assessment configured to cognitively stress the subject (step 304), generate stressed cognitive performance data corresponding to a cognitive performance of the frontal lobe of the subject while stressed based at least in part on a presence or absence of fixation of the one or more eyes of the subject during the cognitive assessment (step 305), and determine brain dysfunction of the subject based at least in part on the baseline cognitive performance data and the stressed cognitive performance data (step 306). The cognitive assessment that is configured to cognitively stress the subject can be configured to stress the frontal lobe of the subject. Alternatively, other type of cognitive stress can be applied through the cognitive assessment. Additionally, although it is the frontal lobe that is stressed during the cognitive assessment, the brain dysfunction that is determined can be any type of dysfunction in other parts of the brain, including multimodal dysfunction or executive dysfunction, which can reside in other parts of the brain (other than the frontal lobe).

The cognitive assessment can be any set of instructions, questions, or commands that are configured to cognitively stress the subject. For example the cognitive assessment can be one or more of a Wisconsin Card Sorting test, a Phonemic Verbal Fluency test, and/or a Stroop Color Word Interference Test, which are all configured to stress the frontal lobe of a subject.

Figure 6A:
FIGS. 6A-6B illustrate an example output of a sequence of assessment images on the neurological screening device according to an exemplary embodiment.
Figure 6B:

In the scenario where there are multiple displays, the controller can be configured to cause output of the plurality of assessment images on the plurality of displays. The controller can be configured to cause output of the plurality of images on the displays concurrently on multiple displays, consecutively one or more displays, or some combination of the two. The controller is configured to cause output of the images on the displays at predetermined times and intervals, depending upon the particular cognitive assessment being performed. FIGS. 6A-6B illustrate an example output of a sequence of assessment images on the neurological screening device according to an exemplary embodiment.

Figure 4:
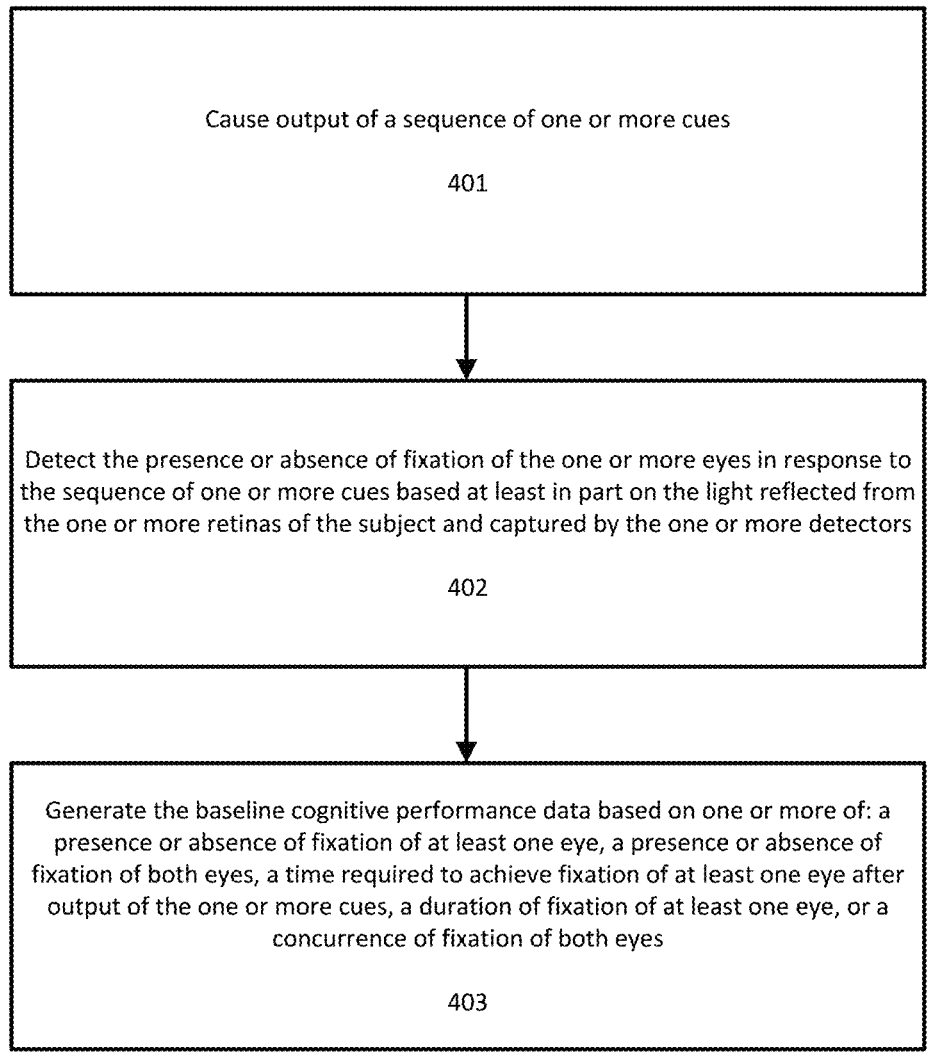
FIG. 4 illustrates a flowchart for generating baseline cognitive performance data corresponding to a baseline cognitive performance of a frontal lobe of a subject according to an exemplary embodiment.

FIG. 4 illustrates a flowchart for generating baseline cognitive performance data corresponding to a baseline cognitive performance of a frontal lobe of a subject according to an exemplary embodiment. Specifically, the controller is configured to cause output of a sequence of one or more cues (step 401), detect the presence or absence of fixation of the one or more eyes in response to the sequence of one or more cues based at least in part on the light reflected from the one or more retinas of the subject and captured by the one or more detectors (step 402), and generate the baseline cognitive performance data based on one or more of a presence or absence of fixation of at least one eye, a presence or absence of fixation of both eyes, a time required to achieve fixation of at least one eye after output of the one or more cues, a duration of fixation of at least one eye, and/or a concurrence of fixation of both eyes (step 403).

Figure 5:
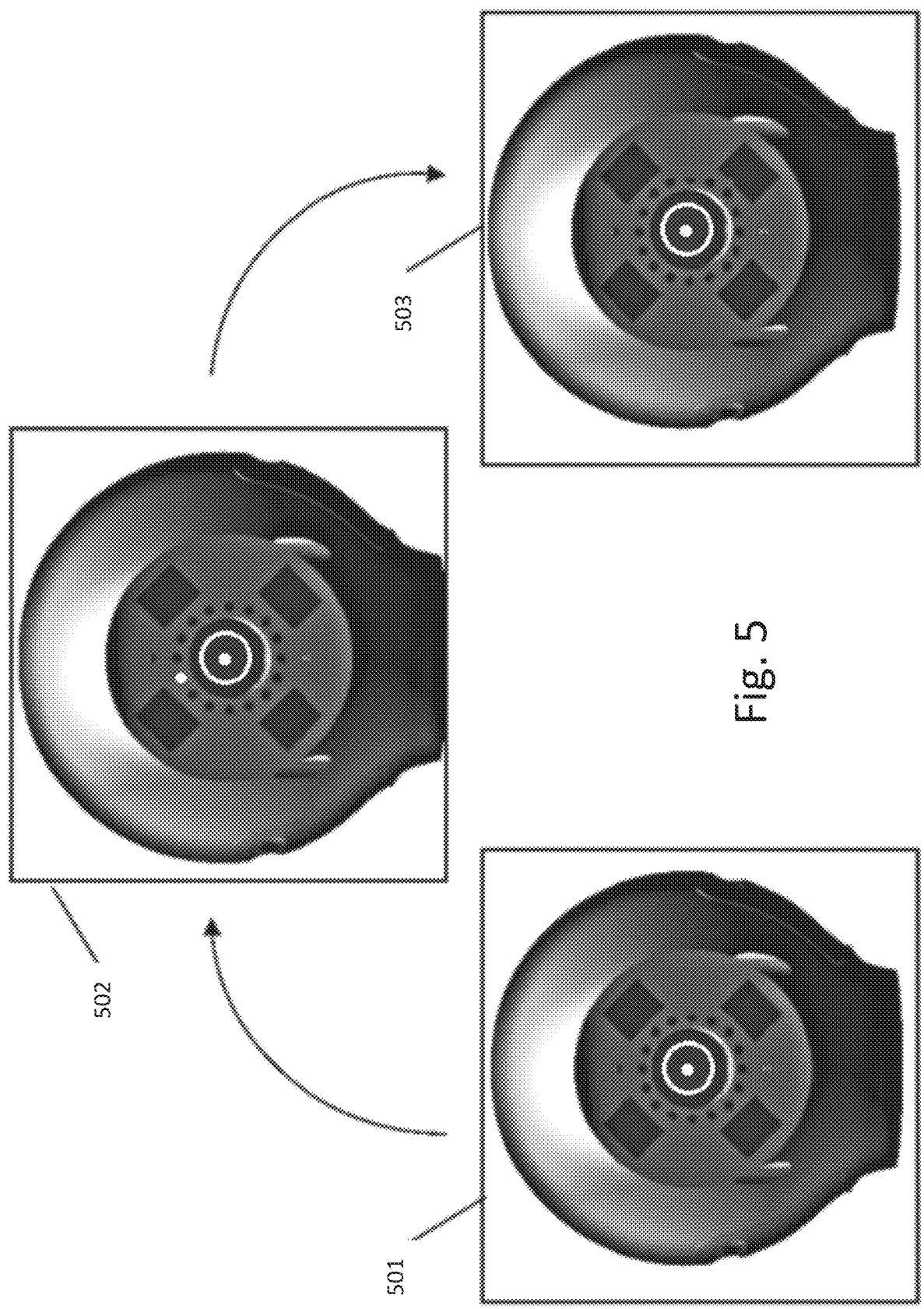
FIG. 5 illustrates an example output of a sequence of cues on the neurological screening device according to an exemplary embodiment.

As discussed above, the neurological screening device can include lights disposed on or in an external surface of the device. In this case, the controller can be configured to cause output of the sequence of one or more cues by activating the one or more lights. FIG. 5 illustrates an example output of a sequence of cues on the neurological screening device according to an exemplary embodiment. As shown in FIG. 5, the neurological screening device initially presents the fixation target (box 501), the fixation target is then removed and a light is activated (box 502), and the light is deactivated and the fixation target is again output (box 503). Alternatively or additionally, the controller can be configured to cause output of the sequence of one or more cues on the one or more displays of the neurological screening device.

The baseline cognitive performance data can include a variety of metrics, including eye fixation, eye convergence, eye binocularity, or eye saccadic latency. Fixation, sometimes referred to as visual fixation or fixation stability, is the maintenance of a visual gaze on a particular location and can be detected using any of the fixation detection techniques discussed earlier in this application. Binocularity, sometimes referred to as binocular alignment is the ability to fixate on an object/location with both eyes and can be detected by checking both eyes of the user for fixation. In ophthalmology, convergence is the simultaneous inward movement of both eyes toward each other, usually in an effort to maintain single binocular vision when viewing an object and can be detected based upon detecting simultaneous movement of both eyes and/or simultaneous achievement of fixation in both eyes. Additionally, saccadic latency corresponds to a delay between the time of appearance of a fixation target and the time required for the eye of the subject to fixate on the target and can be measured by tracking when cues are output, when the fixation target is presented to a subject, and/or when the subject achieves fixation, or by tracking when a cue is output and fixation is lost by a subject. A related measure, saccadic velocity, can also be measured and utilized based upon an angular speed of the eye in achieving fixation after appearance of a target.

FIG. 7 illustrates a flowchart for generating stressed cognitive performance data corresponding to a cognitive performance of a frontal lobe of a subject while stressed according to an exemplary embodiment. The controller is configured to determine a response of the subject to the cognitive assessment based at least in part on a presence or absence of fixation of the one or more eyes, the presence or absence of fixation being determined based at least in part on the light reflected from the one or more retinas of the subject and captured by the one or more detectors (step 701), perform a lookup in a memory of a correct response to the cognitive assessment based at least in part on the plurality of assessment images (step 704); and generate the stressed cognitive performance data based on one or more of: a presence or absence of fixation of at least one eye, a presence or absence of fixation of both eyes, a time required to achieve fixation of at least one eye after output of the plurality of assessment images, a duration of fixation of at least one eye, a concurrence of fixation of both eyes, or a response of the subject to the cognitive assessment in comparison to the correct response (step 705).

Similar to the baseline cognitive performance data, the stressed cognitive performance data can include eye fixation, eye convergence, eye binocularity, or eye saccadic latency/saccadic velocity. Additionally, the stressed cognitive performance data can include a score or other metric representing how well the subject performed on the cognitive assessment. For example, if the cognitive assessment required the subject to respond to 10 sets of images or stimuli, and the subject responded correctly 9 times out of 10, the subject could be assigned a cognitive assessment score of 90 or 90%.

In the scenario where the neurological screening device includes a second projection apparatus, the controller can be configured to use the second projection apparatus to transmit an indication of whether a subject has correctly or incorrectly responded to a cognitive assessment or a stage of a cognitive assessment. This scenario is shown as optional steps 702-703 of FIG. 7. In particular, the controller can be configured to update a second image (that previously displayed nothing or displayed, for example, a fixation target), based at least in part on the response of the subject, the updated second image indicating whether the response of the subject to the cognitive assessment is correct or incorrect (step 702), and to cause the second projection apparatus to project the updated second image (step 703). The controller can be configured to update the second image by selecting an image indicative of a correct response as the second image when the response of the subject matches the correct response or selecting an image indicative of an incorrect response as the second image when the response of the subject does not match the correct response. The images can be selected from a memory of the controller.

Figure 8:
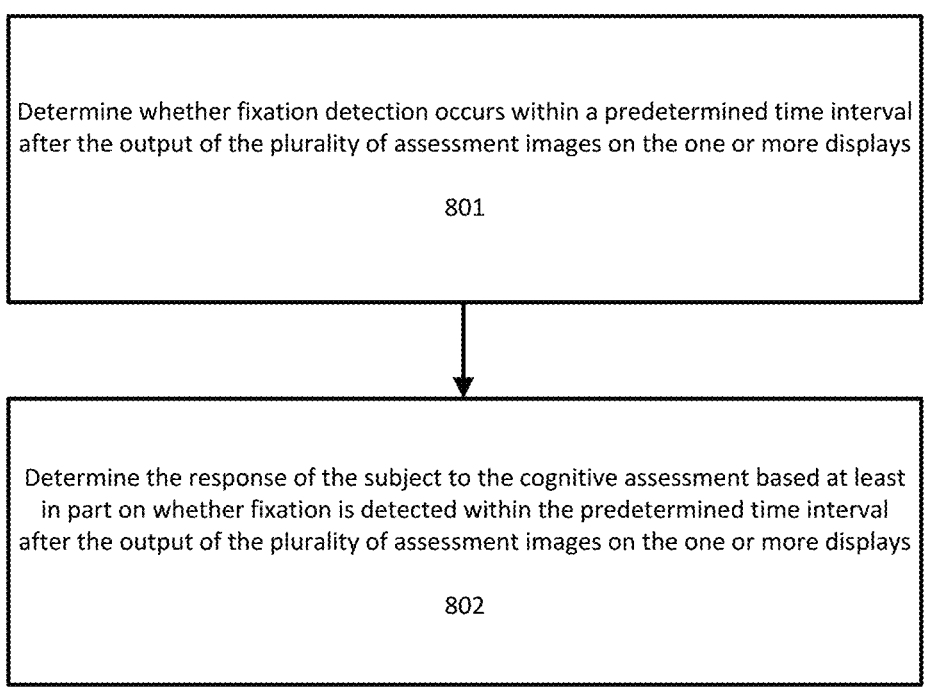
FIG. 8 illustrates a flowchart for determining a response of a subject to a cognitive assessment according to an exemplary embodiment.

FIG. 8 illustrates a flowchart for determining a response of a subject to a cognitive assessment according to an exemplary embodiment. The controller is configured to determine whether fixation detection occurs within a predetermined time interval after the output of the plurality of assessment images on the one or more displays (step 801), and determine the response of the subject to the cognitive assessment based at least in part on whether fixation is detected within the predetermined time interval after the output of the plurality of assessment images on the one or more displays (step 802).

The neurological screening device and method for neurological screening disclosed herein utilize fixation not only as metric for assessing cognitive dysfunction, but also as a means for the subject to convey a response to the tasks, instructions, or queries of the cognitive assessment. In other words, the subject is instructed to fixate on a central target in order to convey a particular response. As described above, the controller is able to parse this fixation in the context of the particular cognitive assessment to determine the subject's response to that cognitive assessment. If fixation occurs within a predetermined time interval after output of a set of assessment images, then the controller can be configured to interpret that fixation as equivalent to a particular verbal answer to that set of assessment images and a query, command, or instruction posed by the cognitive assessment.

Figure 9:
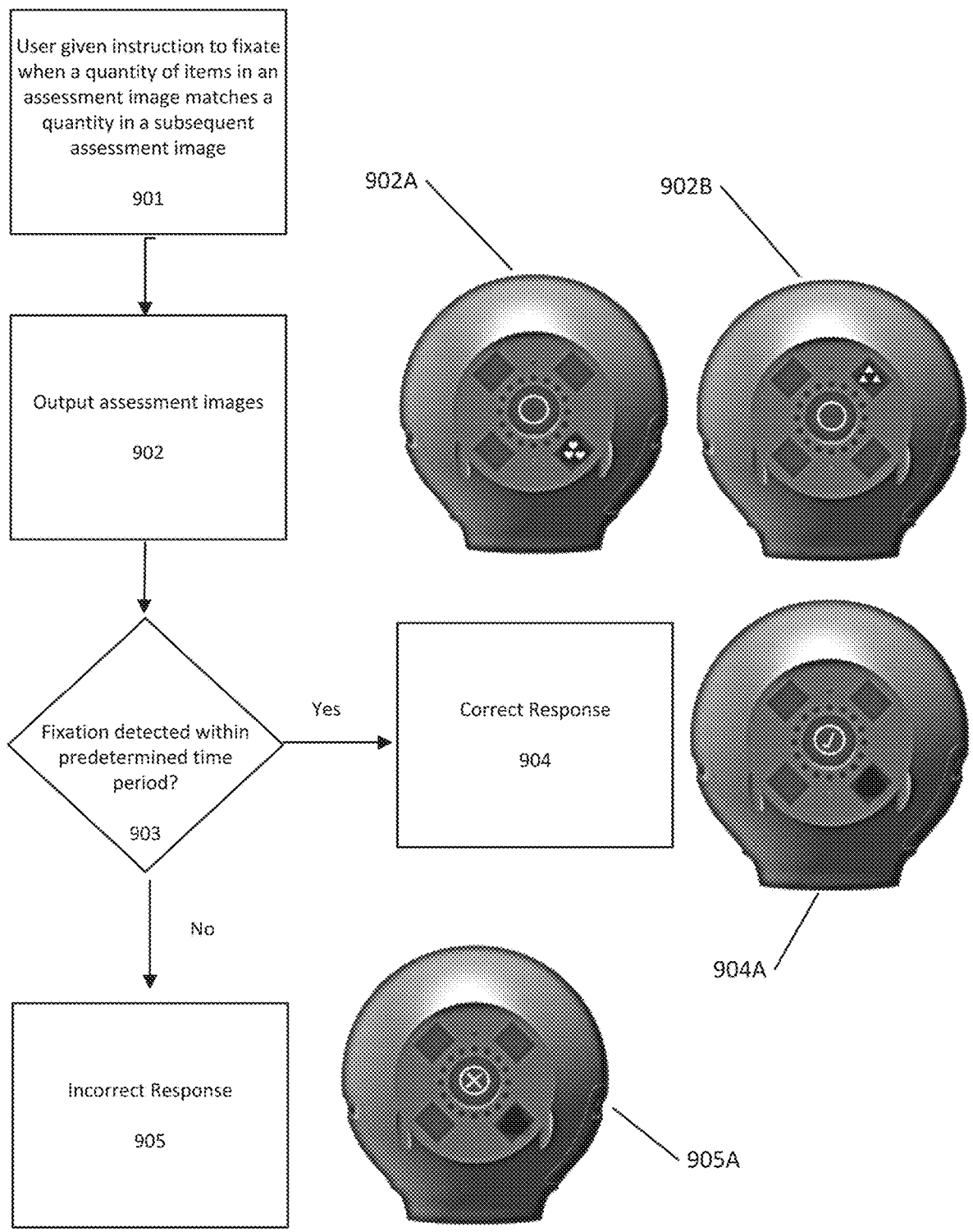
FIG. 9 illustrates a flowchart and example of a cognitive assessment according to an exemplary embodiment.

FIG. 9 illustrates a flowchart and example output of the neurological screening device during a cognitive assessment according to an exemplary embodiment. At step 901 a user is given an instruction to fixate when a quantity of items in an assessment image matches a quantity of items in a subsequent assessment image. At step 902 the assessment images are output. These include an image of three hearts, as shown in box 902A, and a subsequent image of three triangles, shown in box 902B. At step 903 the controller determines whether fixation has been detected within a predetermined time period after the output of the assessment images. If fixation is detected, then at step 904 the controller determines that the correct response was given and outputs a "check" image as the central image (i.e., the second image generated by the second projection apparatus), as shown in box 904A. Otherwise, if fixation is not detected, then at step 905 the controller determines that the incorrect response was given and outputs a "x" image as the central image, as shown in box 905A.

Figure 10:
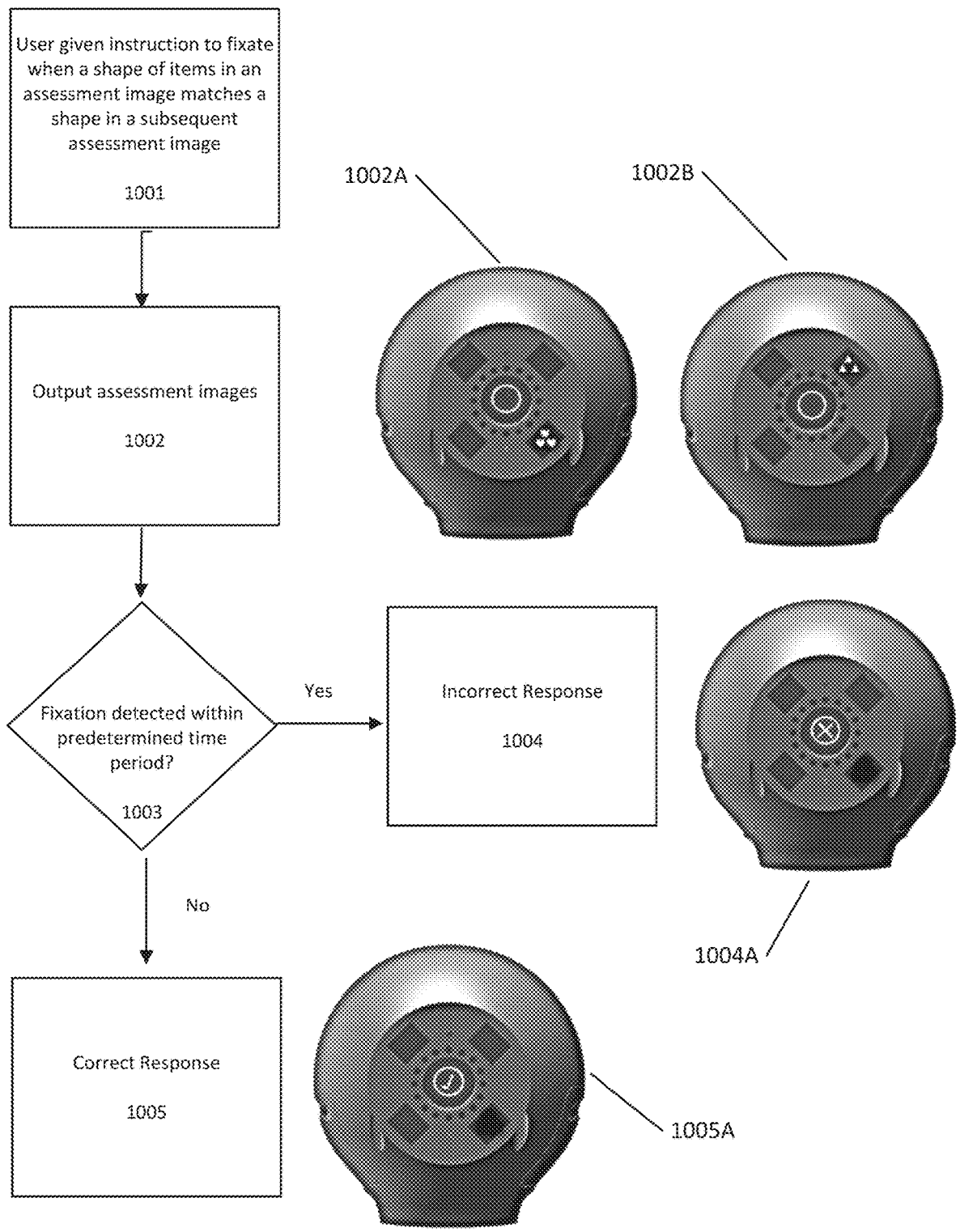
FIG. 10 illustrates a flowchart and example of another cognitive assessment according to an exemplary embodiment.

FIG. 10 illustrates a flowchart and example of another cognitive assessment according to an exemplary embodiment. At step 1001 a user is given an instruction to fixate when a shape of items in an assessment image matches a shape of items in a subsequent assessment image. At step 1002 the assessment images are output. Once again, these include an image of three hearts, as shown in box 1002A, and a subsequent image of three triangles, shown in box 1002B. At step 1003 the controller determines whether fixation has been detected within a predetermined time period after the output of the assessment images. In this case, if fixation is detected, then at step 1004 the controller determines that the incorrect response was given and outputs an "x" image as the central, as shown in box 1004A. Otherwise, if fixation is not detected, then after the predetermined time period passes, at step 1005 the controller determines that the correct response was given and outputs a "check" image as the central image, as shown in box 1005A.

The cognitive assessment can be a multi-stage assessment, requiring the output of multiple sets of assessment images and the repeated collection or generation of stressed cognitive performance data after each stage. In this case the controller can be configured to repeat, for a predetermined quantity of iterations (corresponding to the quantity of stages), the steps of: causing output of a new plurality of assessment images on the one or more displays of the neurological screening device, the plurality of assessment images corresponding to a new stage of the cognitive assessment configured to cognitively stress the subject, and updating the stressed cognitive performance data corresponding to the cognitive performance of the frontal lobe of the subject while stressed based at least in part on a presence or absence of fixation of the one or more eyes during the new stage of the cognitive assessment. This process provides a longitudinal view of the cognitive performance of a subject in response to continued stress on the frontal lobe.

Figure 11:
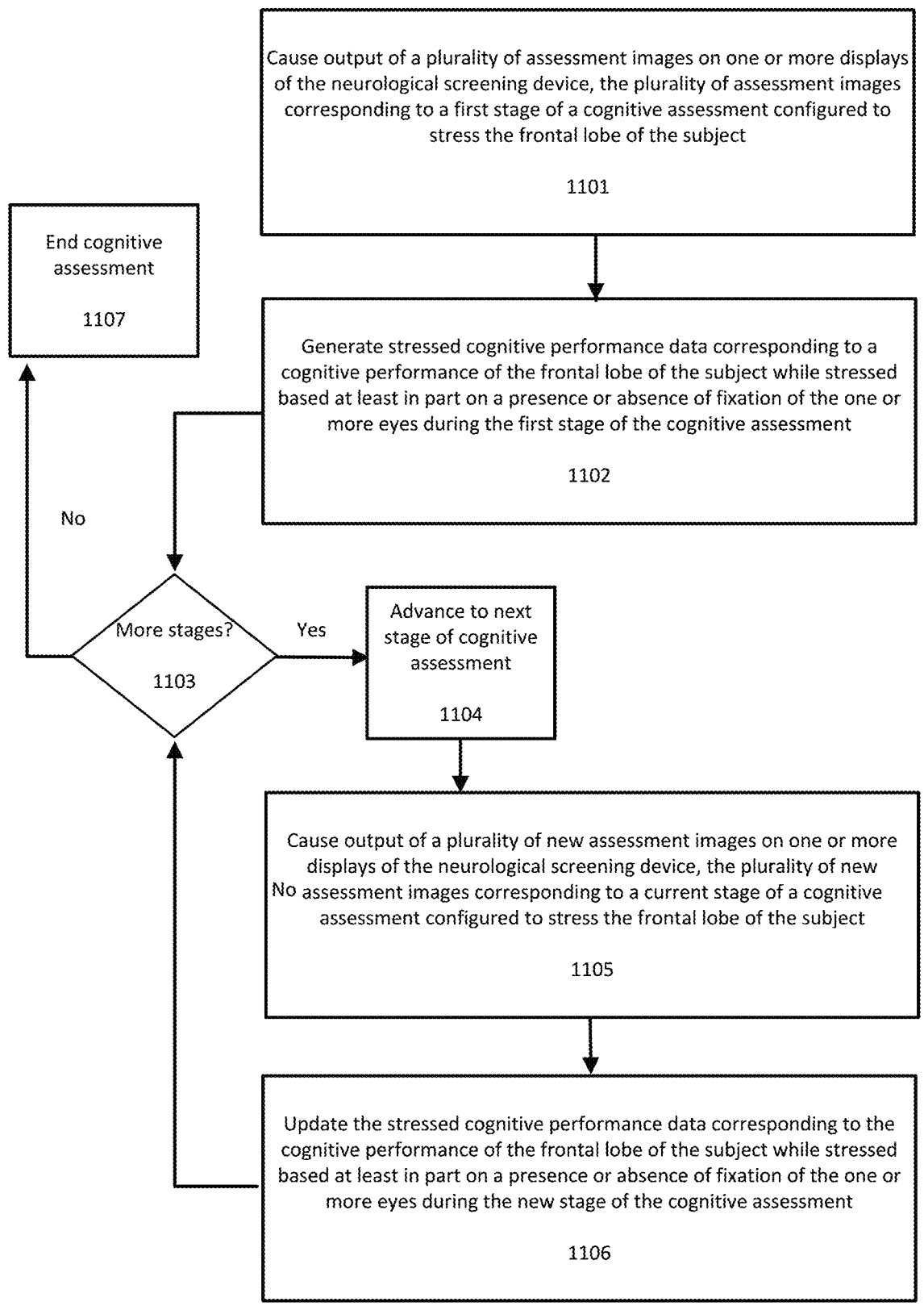
FIG. 11 illustrates a flowchart for performing a multi-stage cognitive assessment using the neurological screening device according to an exemplary embodiment.

FIG. 11 illustrates a flowchart for performing a multi-stage cognitive assessment using the neurological screening device according to an exemplary embodiment. At step 1101 the controller causes output of a plurality of assessment images on one or more displays of the neurological screening device, the plurality of assessment images corresponding to a first stage of a cognitive assessment configured to cognitively stress the subject (e.g., by stressing the frontal lobe of the subject). This step corresponds to step 304 of FIG. 3.

At step 1102 the controller generates stressed cognitive performance data corresponding to a cognitive performance of the frontal lobe of the subject while stressed based at least in part on a presence or absence of fixation of the one or more eyes during the first stage of the cognitive assessment. This step corresponds to step 305 of FIG. 3.

However, rather than proceeding directly to a step of determining brain dysfunction after generating stressed cognitive performance data, as shown in FIG. 3, the multi-stage cognitive assessment first repeats steps 1103-1107 of FIG. 11 for one or more iterations.

At step 1103 the controller determines whether there are more stages remaining in the cognitive assessment. If so, the controller advances the cognitive assessment to the next stage at step 1104. This can be performed, for example, by loading the relevant set of assessment images in memory and/or issuing one or more instructions to the subject.

At step 1105 the controller causes output of a plurality of new assessment images on one or more displays of the neurological screening device, the plurality of new assessment images corresponding to a current stage of a cognitive assessment configured to cognitively stress the subject.

At step 1106 the controller updates the stressed cognitive performance data corresponding to the cognitive performance of the frontal lobe of the subject while stressed based at least in part on a presence or absence of fixation of the one or more eyes during the new stage of the cognitive assessment.

The process then returns to step 1103 and continues to iterate through steps 1104-1106 while there are more stages in the cognitive assessment. When there are no more stages, then the cognitive assessment ends at step 1107 (and brain dysfunction is then determined based upon the baseline cognitive performance data and the updated stressed cognitive performance data).

As discussed previously, when the neurological screening device includes lights, the lights can also be activated as part of the cognitive assessment that is configured to cognitively stress the subject, either alone or in conjunction with the displays. In this case, the controller can be configured to cause activation of the one or more lights as part of the cognitive assessment configured to cognitively stress the subject.

Figure 12:
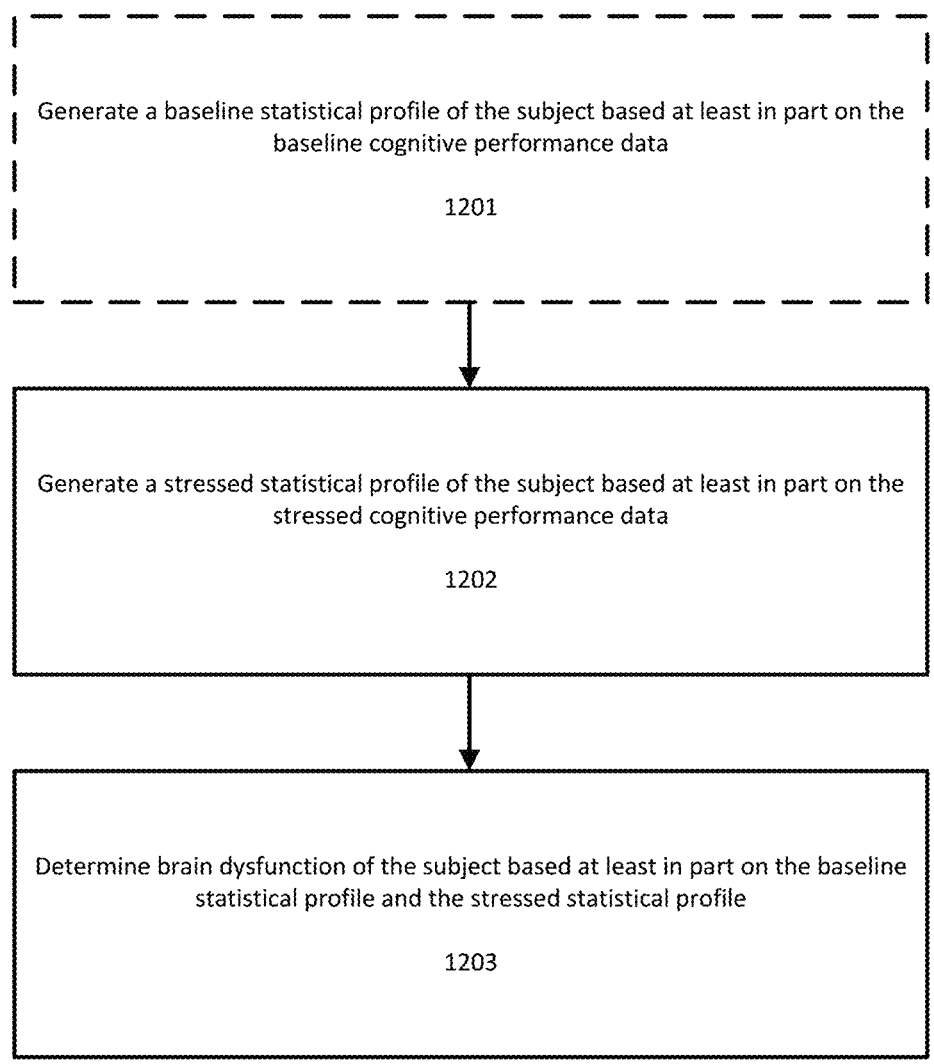
FIG. 12 illustrates a flowchart for performing a neurological screening to assess brain dysfunction according to an exemplary embodiment.

FIG. 12 illustrates a flowchart for performing a neurological screening to assess brain dysfunction according to an exemplary embodiment. At optional step 1201, the controller is configured to generate a baseline statistical profile of the subject based at least in part on the baseline cognitive performance data. In the scenario where baseline cognitive performance data is not generated, this step can be omitted.

At step 1202, the controller is configured to generate a stressed statistical profile of the subject based at least in part on the stressed cognitive performance data.

At step 1203, the controller is configured to determine brain dysfunction of the subject based at least in part on the baseline statistical profile and the stressed statistical profile. As discussed earlier, the brain dysfunction that is determined can be any type of brain dysfunction in any part of the brain, including multimodal dysfunction or executive dysfunction.

In the scenario where the baseline cognitive performance data is not generated, the controller can optionally be configured, at step 1203, to determine brain dysfunction of the subject based at least in part on the stressed statistical profile. This step can include, for example, comparing the stressed statistical profile to stressed statistical profiles of other subjects, to one or more benchmark stressed statistical profiles, or to earlier captured stressed statistical profiles of the same subject.

The optional baseline statistical profile and the stressed statistical profile can be built using a variety of different statistical techniques, statistical models, and/or statistical variables or scores. For example, all of the baseline cognitive performance data can be processed by the controller to generate a single value indicative of the subject's baseline cognitive ability. Similarly, all of the stressed cognitive performance data can be processed by the controller to generate a single value indicative of the subject's stressed cognitive ability. Alternatively, the profiles can store multiple different variables expressing different facets of the subject's baseline and stressed cognitive ability.

The step of determining brain dysfunction, such as frontal lobe dysfunction, of the subject based at least in part on the baseline statistical profile and the stressed statistical profile can include comparing the baseline statistical profile to the stressed statistical profile. This step can further include quantifying the differences between the baseline statistical profile and the stressed statistical profile and then comparing that result to one or more benchmark values in order to determine whether a subject is suffering from brain dysfunction.

Figure 14:
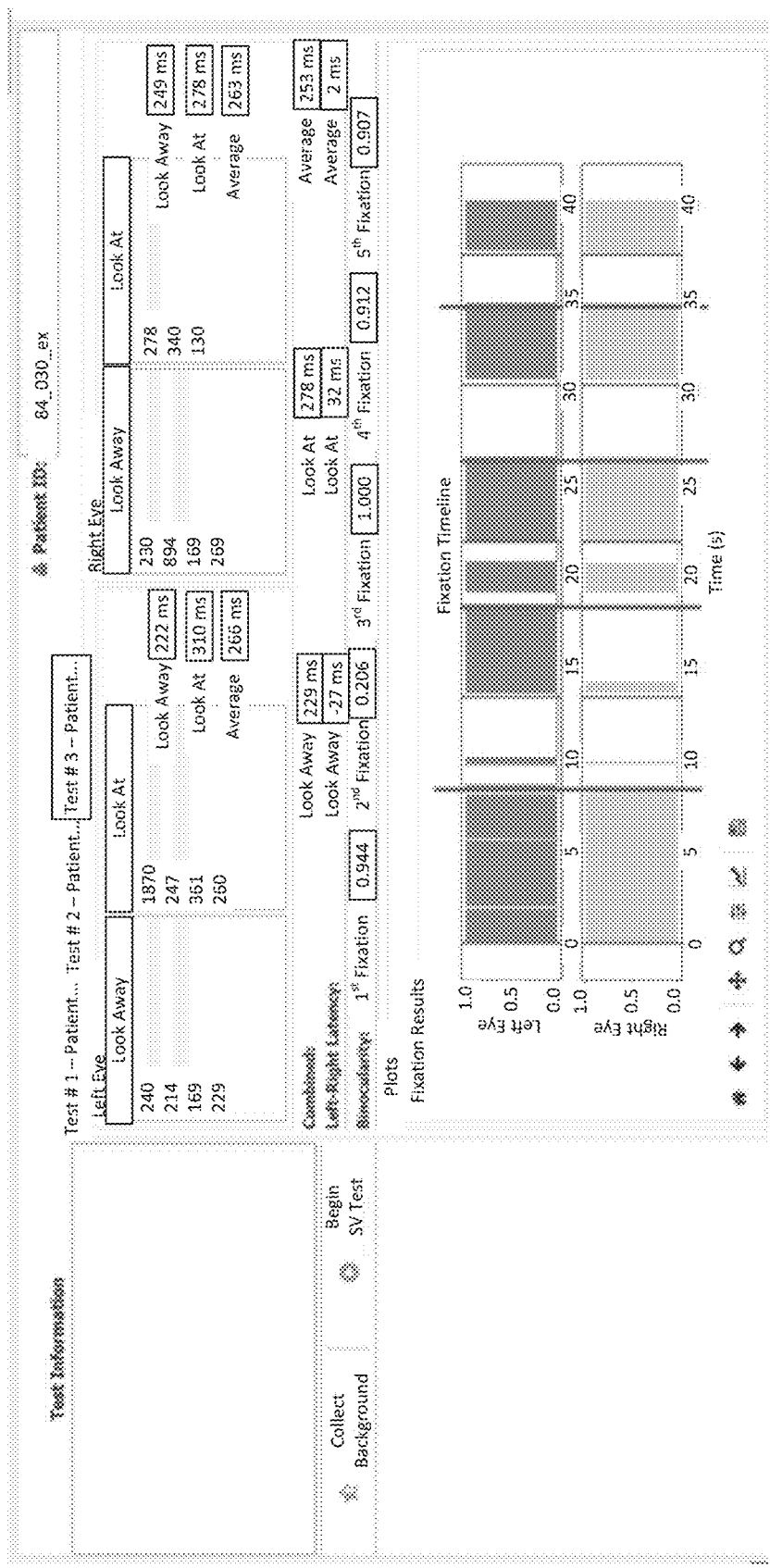
FIG. 14 illustrates an example output screen showing fixation and binocularity statistics for a cognitive assessment according to an exemplary embodiment.

The controller can be configured to output all or a portion of the baseline statistical profile, the stressed statistical profile, or result of the step of determining brain dysfunction of the subject on one or more of the displays of the neurological screening device or on an external display communicatively coupled to the neurological screening device. FIG. 14 illustrates an example output screen showing fixation and binocularity statistics for a cognitive assessment according to an exemplary embodiment.

The controller can further be configured to identify one or more possible health conditions of the subject based at least in part on the determined brain dysfunction. This identification can take the form of a probability distribution or other estimate of a likelihood that a subject is suffering from the one or more possible health conditions. The possible health conditions can include, for example, brain trauma, impeded brain function, brain injury, strabismus, ocular motor apraxia, and/or amblyopia.

As discussed previously, numerous cognitive assessments can be efficiently performed using the neurological screening device disclosed herein. The following sections discuss some common cognitive assessments used to screen for frontal lobe dysfunction and provide examples of implementation on the disclosed neurological screening device.

Evaluation of frontal lobe function conventionally relies on neuropsychological tests such as the Wisconsin Card Sorting Test and the Stroop Word Test. These and other tests target frontal lobe-associated executive functions that control ("supervise") lower level cognitive processing in the service of goal-directed behavior. Frontal lobe-linked executive functions include specific cognitive processes such as working memory (especially "updating"), response inhibition, interference control, and set shifting. Commonly deployed neuropsychological tests of frontal executive functioning include the Wisconsin Card Sorting Test, Phonemic Verbal Fluency, and Stroop Color Word Interference Test.

These tests are typically configured such that a patient is requested to verbally perform a specified task, or alternatively, utilize a computer to respond to test items. These tests are time consuming, subject to a multitude of clinical confounds, and are not coupled to objective measures of neurophysiological performance targeting oculomotor function, coordination, and control.

For Wisconsin Card Sorting Test (WCST), the subject is asked to match a primary card with one of four cards in a grouping based on one of three distinct attribute categories (color, quantity, shape). Both the primary card and grouping categories can be altered during the task. The challenge with Wisconsin Card Sorting is that the directions regarding the active match rule is not explicitly shared with the test-taker (subject). Rather, the subject is informed whether a given choice is correct or not, and thus must learn by trial-and-error inference whether the active matching rule involves color, shape, or quantity. As the test progresses (typically over the course of 10-20 minutes), the evaluator (or software program algorithm) changes the matching rule without conveying the new correct category other than by indicating whether or not the subject's responses are correct. Category switching is typically conducted at multiple times and random intervals during a given test session.

A test session begins by informing the subject that she will be presented with a target (stimulus) card and then asked to match the target card with other cards based on an unstated category (i.e., color, shape, quantity). Feedback to the subject is limited to indicating whether a particular match is correct or not. For example, a test may begin with an unstated rule of matching colors (e.g., red). In this case, a stimulus card showing two red crosses would be correctly matched by the card with the red circle, but not by cards with any other color (e.g., green stars, blue squares, yellow crosses). At a given point in the test after the subject has demonstrated mastery of the initial matching rule, the examiner (or program) changes the matching rule (e.g., from red to crosses) without informing the test subject other than by indicating whether subsequent matching choices are correct or not. In this example, if the subject now matches to a red card, the examiner (or program) would indicate an incorrect choice. In a subject with intact frontal lobe function, successive incorrect matches should quickly elicit correct responses consistent with rule switching (set shifting). However, subjects with impaired frontal lobe function show deficits in this task by perseverating with previous responses despite cueing that doing so is now incorrect.

The Stroop Color Word Interference Test is another widely used test to evaluate related cognitive functions. This test can be administered in multiple ways. In one common format, the test-taker is presented with a series of cards in which the written word and text color semantically conflict. The test-taker is asked to respond to one category that is in semantic conflict with the other presented categories. Cognitive interference ("Stroop Effect") can be detected as delayed response time (correct response) or matching error (incorrect response).

The test-taker may be asked to speak out the color of a word, while the written word is a different color. For example, the word RED may be written in blue font. The correct response would be blue. Tasks could vary to ask them to read the word rather than the color of the font, or to only read words of certain colors, etc.

Both tests (WCST, Stroop) are useful tools to objectively assess cognitive function in the face of set shifting (WCST) or conflicting information (Stroop). Normal performance in the WCST and Stroop tests requires cognitive flexibility and functionally intact frontal lobes. Individuals with transient or permanent damage to the frontal lobes and allied brain regions demonstrate deficits in these and related tasks. These tests are also useful in detecting alterations in brain structure or function that underpin attention, working memory, response inhibition, abstraction, and executive function.

Figure 13:
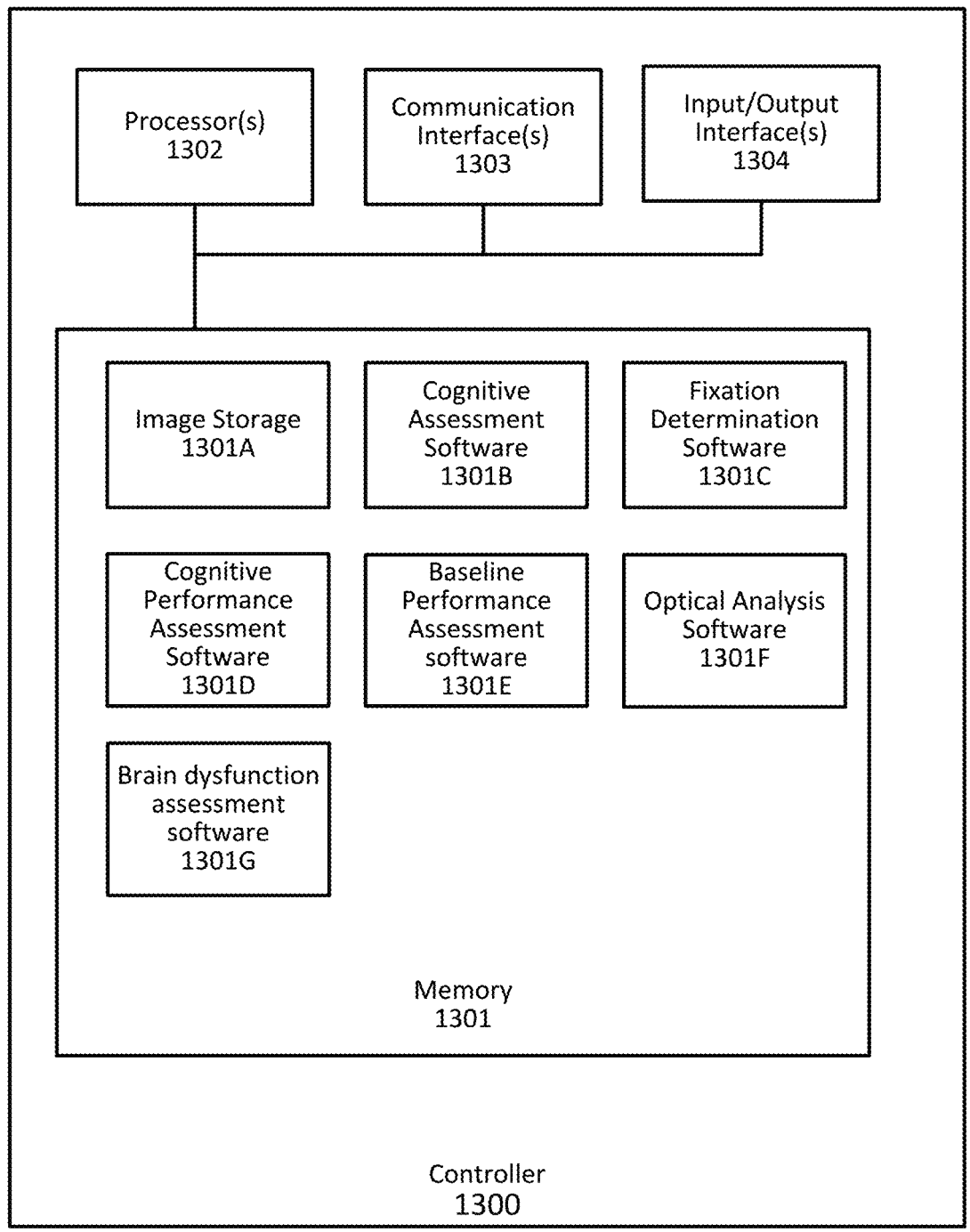
FIG. 13 illustrates the components of the specialized controller of the neurological screening device.

An example of how a typical test may be conducted on a test subject using the disclosed neurological screening device is described below:

The patient will be instructed to follow a light with their eyes;

A centrally-located fixation target will illuminate for a randomly generated length of time (between 0.1 and 10 secs);

The fixation target will turn off;

A new, randomly-located, illuminated target will appear for a randomly-generated length of time (between 0.1 and 10 secs);

The newly illuminated target will turn off;

Either the original fixation target, or yet another randomly-located, illuminated target will appear for a randomly generated length of time (between 0.1 and 10 secs). This cycle will continue for approximately 30 seconds;

The patient will be instructed to look at two screens on the device and to then look at the fixation target on the device when the subject identifies a perceived match;

The patient may be asked to match: color, quantity, shape, size, etc.;

If the patient fixates on a target that correctly identifies a match, then a symbol will appear in the field of view to indicate that the match is correct;

If the patient looks at the fixation target when the screens DO NOT match, then a symbol will appear to alert the patient that the perceived match is incorrect;

The two screens will change images at randomly generated times (between 0.1 and 10 secs) in order to increase cognitive stress on frontal lobe function;

FIG. 13 illustrates the components of the specialized controller 1300 of the neurological screening device. Specialized controller 1300 is a computing device that includes a memory 1301 that is a non-transitory computer-readable medium and can be volatile memory (e.g., registers, cache, RAM), non-volatile memory (e.g., ROM, EEPROM, flash memory, etc.), or some combination of the two.

As shown in FIG. 13, memory 1301 includes an image storage 1301A that can store the assessment images as well as any images captures by the neurological screening device in the course of a screening. Memory also includes cognitive assessment software 1301B that stores cognitive assessments, links to images in image store, and associated instructions, fixation determination software 1301C, cognitive performance assessment software 1301D, baseline performance assessment software 1301E, optical analysis software 1301F, and brain dysfunction assessment software 1301G. Each of the software components in memory 1301 store specialized instructions and data structures configured to perform the cognitive assessment administration, cognitive assessment performance analysis, baseline performance analysis, fixation determination, optical analysis, and brain and frontal lobe dysfunction assessment techniques described herein.

All of the software stored within memory 1301 can be stored as a computer-readable instructions, that when executed by one or more processors 1302, cause the processors to perform the functionality described with respect to FIGS. 1-12.

Processor(s) 1302 execute computer-executable instructions and can be a real or virtual processors. In a multi-processing system, multiple processors or multicore processors can be used to execute computer-executable instructions to increase processing power and/or to execute certain software in parallel.

Controller 1300 additionally includes a communication interface 1303, such as a network interface, which is used to communicate with devices, applications, or processes on a computer network or computing system, collect data from devices on a network, and implement encryption/decryption actions on network communications within the computer network or on data stored in databases of the computer network. The communication interface conveys information such as computer-executable instructions, audio or video information, or other data in a modulated data signal. A modulated data signal is a signal that has one or more of its characteristics set or changed in such a manner as to encode information in the signal. By way of example, and not limitation, communication media include wired or wireless techniques implemented with an electrical, optical, RF, infrared, acoustic, or other carrier.

Controller 1300 further includes input and output interfaces 1304 that allow users (such as system administrators) to provide input to the controller to cause the neurological screening device to display information, to edit data stored in memory 1301, or to perform other administrative functions. For example, an administrator can configure, add, or edit cognitive assessments stored in memory 1301.

An interconnection mechanism (shown as a solid line in FIG. 13), such as a bus, controller, or network interconnects the components of the computing environment 1300.

Input and output interfaces 1304 can be coupled to input and output devices. For example, the neurological screening device can be configured to have Universal Serial Bus (USB) ports to allow for the connection of a keyboard, mouse, pen, trackball, touch screen, or game controller, a voice input device, a scanning device, a digital camera, remote control, or another device that provides input to the computing environment.

Input/output interfaces can connect the controller 1300 to the other components of the neurological screening device, including the displays, the lights, the detectors, the projection apparatus and/or the second projection apparatus.

The controller 1300 can additionally utilize a removable or non-removable storage, such as magnetic disks, magnetic tapes or cassettes, CD-ROMs, CD-RWs, DVDs, USB drives, or any other medium which can be used to store information and which can be accessed within the controller 1300.

Optionally, part of the functionality performed by the controller 1300 can be performed by one or more computing devices located external to the housing. In this case, communication interface 1303 can be used to communicate with external devices. For example, resource-intensive statistical processing used to determine brain dysfunction can be outsourced to an external computing device(s), server(s), or cloud network and the results can be returned to the controller from the external device via the communication interface 1303.

The disclosed neurological screening device and method for neurological screening enable the frontal lobe to be stressed while performing a series of frontal lobe-dependent tasks in the cognitive assessments that are specifically devised to require ocular responses. As discussed above, the tasks include identifying matching symbols, shapes, or quantities that appear on the display(s), or alternatively, avoiding responses to a previously presented choices or interfering stimulus.

Correct or incorrect matching responses in these cognitive assessment as well as the measurements of fixation, convergence, binocularity, saccadic latency, and other ocular metrics of the test subject provide clinicians with information to assess brain health and function, and with repeated testing, the ability to track recovery.

The disclosed neurological screening device and neurological screening method combines binocularity and other optical metric testing with a cognitive "stress test" component that tasks frontal lobe function. Neural substrates underpinning ocular binocularity and higher-order cognitive tasks both rely on intact frontal lobe function. By placing cognitive demand on this brain region, the disclosed neurological screening device enables objective detection and assessment of brain dysfunction associated with disease, injury, medical or metabolic disturbance(s), drug-related or toxic exposure(s), or other condition(s) that transiently or permanently impair central nervous system (CNS) function.

Specifically, test performance (i.e., ocular binocularity and cognitive performance) is automatically determined and analyzed by the instrument using retinal birefringence scanning to determine the point on the instrument screen where the test subject's eyes should fixate for each match and compared to where the subject's eyes actually fixate. Saccadic latency and binocularity are also automatically determined through the time for each eye to fixate or lose fixation and the fixation point of each eye on the test screen. Retinal birefringence scanning to determine fixation and loss of fixation can be accomplished in the manner described in U.S. patent application Ser. No. 16/354,749, titled "APPARATUS AND METHOD FOR OPHTHALMIC NEURAL SCANNING," the disclosure of which is hereby incorporated by reference in its entirety.

In addition, the device can measure various metrics related to cognitive performance including (but limited to): perseverative errors, non-perseverative errors, number of categories achieved, failure to maintain set, trials to complete first set, reward sensitivity, punishment sensitivity, decision consistency, attentional focusing. Temporal metrics associated with these cognitive performance metrics are also automatically acquired.

It will be appreciated by those skilled in the art that changes could be made to the embodiments described above without departing from the broad inventive concept thereof. For example, the steps or order of operation of one of the above-described methods could be rearranged or occur in a different series, as understood by those skilled in the art. It is understood, therefore, that this disclosure is not limited to the particular embodiments disclosed, but it is intended to cover modifications within the spirit and scope of the present disclosure.

The invention claimed is:

1. A neurological screening device for assessing brain dysfunction of a subject, the device comprising:
   a projection apparatus configured to project an image onto one or more retinas of one or more eyes of the subject;
   one or more detectors configured to capture light reflected from the one or more retinas of the subject, the reflected light indicating a fixation of the one or more eyes; and
   a controller configured to:
      cause output of a plurality of assessment images on one or more displays of the neurological screening device, the plurality of assessment images corresponding to a cognitive assessment configured to cognitively stress the subject;

generate stressed cognitive performance data corresponding to a cognitive performance of the frontal lobe of the brain of the subject while stressed based at least in part on a presence or absence of the fixation of the one or more eyes during the cognitive assessment; and determine the brain dysfunction of the subject based at least in part on the stressed cognitive performance data of the frontal lobe.

2. The neurological screening device of claim 1, wherein the controller is further configured to generate baseline cognitive performance data corresponding to a baseline cognitive performance of the frontal lobe of the brain of the subject based at least in part on the presence or the absence of the fixation of the one or more eyes and wherein determining the brain dysfunction of the subject based at least in part on the stressed cognitive performance data of the frontal lobe comprises:

determining the brain dysfunction of the subject based at least in part on the baseline cognitive performance data and the stressed cognitive performance data of the frontal lobe.

3. The neurological screening device of claim 2, wherein the controller is configured to generate the baseline cognitive performance data corresponding to the baseline cognitive performance of the frontal lobe of the subject based at least in part on the presence or the absence of the fixation of the one or more eyes by:

causing output of a sequence of one or more cues;

detecting the presence or the absence of the fixation of the one or more eyes in response to the sequence of one or more cues based at least in part on the light reflected from the one or more retinas of the subject and captured by the one or more detectors; and generating the baseline cognitive performance data based at least in part on the presence or the absence of the fixation of the one or more eye and one or more of: the presence or the absence of the fixation of both eyes, a time required to achieve the fixation of at least one eye after the output of the one or more cues, a duration of the fixation of the at least one eye, or a concurrence of the fixation of both eyes.

4. The neurological screening device of claim 3, wherein the controller is configured to cause the output of the sequence of one or more cues on the one or more displays of the neurological screening device.

5. The neurological screening device of claim 3, further comprising one or more lights disposed on or in an external surface of the neurological screening device, wherein the controller is configured to cause the output of the sequence of one or more cues by activating the one or more lights.

6. The neurological screening device of claim 2, wherein the baseline cognitive performance data comprises the fixation of the one or more eyes and one or more of: eye convergence, eye binocularity, or eye saccadic latency.

7. The neurological screening device of claim 2, wherein the controller is configured to determine the brain dysfunction of the subject by:

generating a baseline statistical profile of the subject based at least in part on the baseline cognitive performance data;

generating a stressed statistical profile of the subject based at least in part on the stressed cognitive performance data; and determining the brain dysfunction of the subject based at least in part on the baseline statistical profile and the stressed statistical profile.

8. The neurological screening device of claim 1, wherein the projection apparatus is positioned within a housing of the neurological screening device and configured to project the image through a window of the housing.

9. The neurological screening device of claim 1, wherein the one or more displays of the neurological screening device comprise a plurality of displays and wherein the controller is configured to cause the output of the plurality of assessment images on the plurality of displays.

10. The neurological screening device of claim 1, wherein the controller is configured to generate the stressed cognitive performance data corresponding to the cognitive performance of the frontal lobe of the subject while stressed based at least in part on the presence or the absence of the fixation of the one or more eyes during the cognitive assessment by:

determining a response of the subject to the cognitive assessment based at least in part on the presence or the absence of the fixation of the one or more eyes, the presence or the absence of the fixation being determined based at least in part on the light reflected from the one or more retinas of the subject and captured by the one or more detectors;

performing a lookup in a memory of a correct response to the cognitive assessment based at least in part on the plurality of assessment images; and generating the stressed cognitive performance data based on the presence or the absence of the fixation of the one or more eyes and one or more of: the presence or the absence of the fixation of both eyes, a time required to achieve the fixation of at least one eye after the output of the plurality of assessment images, a duration of the fixation of the at least one eye, a concurrence of the fixation of both eyes, or the response of the subject to the cognitive assessment in comparison to the correct response.

11. The neurological screening device of claim 10, further comprising a second projection apparatus configured to project a second image that is configured to appear to the subject to be centered within the first image and wherein the controller is further configured to:

update the second image based at least in part on the response of the subject, the updated second image indicating whether the response of the subject to the cognitive assessment is correct or incorrect; and cause the second projection apparatus to project the updated second image.

12. The neurological screening device of claim 11, wherein the controller is configured to update the second image based at least in part on the response of the subject by:

selecting an image indicative of a correct response as the second image when the response of the subject matches the correct response; or selecting an image indicative of an incorrect response as the second image when the response of the subject does not match the correct response.

13. The neurological screening device of claim 10, wherein the controller is configured to determine the response of the subject to the cognitive assessment by:

determining whether fixation detection occurs within a predetermined time interval after the output of the plurality of assessment images on the one or more displays; and determining the response of the subject to the cognitive assessment based at least in part on whether the fixation is detected within the predetermined time interval after the output of the plurality of assessment images on the one or more displays.

14. The neurological screening device of claim 1, wherein the stressed cognitive performance data comprises the fixation of the one or more eyes and one or more of: eye convergence, eye binocularity, eye saccadic latency, or a cognitive score on the cognitive assessment.

15. The neurological screening device of claim 1, wherein the plurality of assessment images correspond to a stage of the cognitive assessment and wherein the controller is further configured to repeat, for a predetermined quantity of iterations, the steps of:
   causing output of a new plurality of assessment images on the one or more displays of the neurological screening device, the new plurality of assessment images corresponding to a new stage of the cognitive assessment configured to cognitively stress the subject; and
   update the stressed cognitive performance data corresponding to the cognitive performance of the frontal lobe of the subject while stressed based at least in part on the presence or the absence of the fixation of the one or more eyes during the new stage of the cognitive assessment.

16. The neurological screening device of claim 1, further comprising one or more lights disposed on or in an external surface of the neurological screening device, wherein the controller is further configured to:
   cause activation of the one or more lights as part of the cognitive assessment configured to cognitively stress the subject.

17. The neurological screening device of claim 1, wherein the controller is configured to determine the brain dysfunction of the subject by:
   generating a stressed statistical profile of the subject based at least in part on the stressed cognitive performance data; and
   determining the brain dysfunction of the subject based at least in part on the stressed statistical profile.

18. The neurological screening device of claim 1, wherein the controller is further configured to:
   identify one or more possible health conditions of the subject based at least in part on the determined brain dysfunction.

19. The neurological screening device of claim 18, wherein the one or more possible health conditions comprise one or more of: brain trauma, impeded brain function, brain injury, strabismus, ocular motor apraxia, or amblyopia.

20. The neurological screening device of claim 1, wherein the cognitive assessment comprises one of: a Wisconsin Card Sorting test, a Phonemic Verbal Fluency test, and a Stroop Color Word Interference Test.

21. The neurological screening device of claim 1, wherein the cognitive assessment is configured to stress the frontal lobe of the subject.

22. A neurological screening method for assessing brain dysfunction of a subject with a neurological screening device, the method comprising:
   projecting, by a projection apparatus of the neurological screening device, an image onto one or more retinas of one or more eyes of the subject;
   capturing, by one or more detectors of the neurological screening device, light reflected from the one or more retinas of the subject, the reflected light indicating a fixation of the one or more eyes;
   causing output, by the controller of the neurological screening device, of a plurality of assessment images on one or more displays of the neurological screening device, the plurality of assessment images corresponding to a cognitive assessment configured to cognitively stress the subject;
   generating, by the controller of the neurological screening device, stressed cognitive performance data corresponding to a cognitive performance of the frontal lobe of the brain of the subject while stressed based at least in part on a presence or absence of the fixation of the one or more eyes during the cognitive assessment; and
   determining, by the controller of the neurological screening device, the brain dysfunction of the subject based at least in part on the stressed cognitive performance data of the frontal lobe.

23. The neurological screening method of claim 22, further comprising generating, by the controller of the neurological screening device, baseline cognitive performance data corresponding to a baseline cognitive performance of the frontal lobe of the brain of the subject based at least in part on the presence or the absence of the fixation of the one or more eyes, wherein determining, by the controller of the neurological screening device, the brain dysfunction of the subject based at least in part on the stressed cognitive performance data of the frontal lobe comprises:
   determining the brain dysfunction of the subject based at least in part on the baseline cognitive performance data and the stressed cognitive performance data of the frontal lobe.

24. The neurological screening method of claim 23, wherein generating, by the controller of the neurological screening device, baseline cognitive performance data corresponding to a baseline cognitive performance of the frontal lobe of the subject based at least in part on the presence or the absence of the fixation of the one or more eyes comprises:
   causing output of a sequence of one or more cues;
   detecting the presence or the absence of the fixation of the one or more eyes in response to the sequence of one or more cues based at least in part on the light reflected from the one or more retinas of the subject and captured by the one or more detectors; and
   generating the baseline cognitive performance data based at least in part on the presence or the absence of the fixation of the one or more eye and one or more of: the presence or the absence of the fixation of both eyes, a time required to achieve the fixation of at least one eye after the output of the one or more cues, a duration of the fixation of the at least one eye, or a concurrence of the fixation of both eyes.

25. The neurological screening method of claim 24, wherein the controller is configured to cause the output of the sequence of one or more cues on the one or more displays of the neurological screening device.

26. The neurological screening device of claim 24, further comprising one or more lights disposed on or in an external surface of the neurological screening device, wherein the controller is configured to cause the output of the sequence of one or more cues by activating the one or more lights.

27. The neurological screening method of claim 23, wherein the baseline cognitive performance data comprises the fixation of the one or more eyes and one or more of: eye convergence, eye binocularity, or eye saccadic latency.

28. The neurological screening method of claim 23, wherein determining, by the controller of the neurological screening device, the brain dysfunction of the subject based at least in part on the baseline cognitive performance data and the stressed cognitive performance data of the frontal lobe comprises:
generating a baseline statistical profile of the subject based at least in part on the baseline cognitive performance data;
generating a stressed statistical profile of the subject based at least in part on the stressed cognitive performance data; and
determining the brain dysfunction of the subject based at least in part on the baseline statistical profile and the stressed statistical profile.

29. The neurological screening method of claim 23, wherein determining, by the controller of the neurological screening device, the brain dysfunction of the subject based at least in part on the baseline cognitive performance data and the stressed cognitive performance data of the frontal lobe comprises:
generating a stressed statistical profile of the subject based at least in part on the stressed cognitive performance data; and
determining the brain dysfunction of the subject based at least in part on the stressed statistical profile.

30. The neurological screening method of claim 22, wherein the projection apparatus is positioned within a housing of the neurological screening device and configured to project the image through a window of the housing.

31. The neurological screening method of claim 22, wherein the one or more displays of the neurological screening device comprise a plurality of displays and wherein the controller is configured to cause the output of the plurality of assessment images on the plurality of displays.

32. The neurological screening method of claim 22, wherein generating, by the controller of the neurological screening device, the stressed cognitive performance data corresponding to the cognitive performance of the frontal lobe of the subject while stressed based at least in part on the presence or the absence of the fixation of the one or more eyes during the cognitive assessment comprises:
determining a response of the subject to the cognitive assessment based at least in part on the presence or the absence of the fixation of the one or more eyes, the presence or absence of fixation being determined based at least in part on the light reflected from the one or more retinas of the subject and captured by the one or more detectors;
performing a lookup in a memory of a correct response to the cognitive assessment based at least in part on the plurality of assessment images; and
generating the stressed cognitive performance data based on the presence or the absence of the fixation of the one or more eyes and one or more of: the presence or the absence of the fixation of both eyes, a time required to achieve the fixation of at least one eye after the output of the plurality of assessment images, a duration of the fixation of the at least one eye, a concurrence of the fixation of both eyes, or the response of the subject to the cognitive assessment in comparison to the correct response.

33. The neurological screening method of claim 32, further comprising a second projection apparatus configured to project a second image that is configured to appear to the subject to be centered within the first image and further comprising:

projecting, by the second projection apparatus of the neurological screening device, the second image that is configured to appear to the subject to be centered within the first image;
updating, by the controller of the neurological screening device, the second image based at least in part on the response of the subject, the updated second image indicating whether the response of the subject to the cognitive assessment is correct or incorrect; and
causing, by the controller of the neurological screening device, the second projection apparatus to project the updated second image.

34. The neurological screening device of claim 33, wherein updating, by the controller of the neurological screening device, the second image based at least in part on the response of the subject comprises:
selecting an image indicative of a correct response as the second image when the response of the subject matches the correct response; or
selecting an image indicative of an incorrect response as the second image when the response of the subject does not match the correct response.

35. The neurological screening method of claim 32, wherein determining the response of the subject to the cognitive assessment based at least in part on the presence or the absence of the fixation of the one or more eyes comprises:
determining whether fixation detection occurs within a predetermined time interval after the output of the plurality of assessment images on the one or more displays; and
determining the response of the subject to the cognitive assessment based at least in part on whether the fixation is detected within the predetermined time interval after the output of the plurality of assessment images on the one or more displays.

36. The neurological screening method of claim 22, wherein the stressed cognitive performance data comprises the fixation of the one or more eyes and one or more of: eye convergence, eye binocularity, eye saccadic latency, or a cognitive score on the cognitive assessment.

37. The neurological screening method of claim 22, wherein the plurality of assessment images correspond to a stage of the cognitive assessment and further comprising, repeating, for a predetermined quantity of iterations, the steps of:
causing, by the controller of the neurological screening device, output of a new plurality of assessment images on the one or more displays of the neurological screening device, the new plurality of assessment images corresponding to a new stage of the cognitive assessment configured to cognitively stress the subject; and
updating, by the controller of the neurological screening device, the stressed cognitive performance data corresponding to the cognitive performance of the frontal lobe of the subject while stressed based at least in part on the presence or the absence of the fixation of the one or more eyes during the new stage of the cognitive assessment.

38. The neurological screening method of claim 22, further comprising:
cause, by the controller of the neurological screening device, activation of one or more lights disposed on or in an external surface of the neurological screening device as part of the cognitive assessment configured to cognitively stress the subject.

39. The neurological screening method of claim 22, further comprising:
  identifying, by the controller of the neurological screening device, one or more possible health conditions of the subject based at least in part on the determined brain dysfunction.

40. The neurological screening method of claim 39, wherein the one or more possible health conditions comprise one or more of: brain trauma, impeded brain function, brain injury, strabismus, ocular motor apraxia, or amblyopia.

41. The neurological screening method of claim 22, wherein the cognitive assessment comprises one of: a Wisconsin Card Sorting test, a Phonemic Verbal Fluency test, and a Stroop Color Word Interference Test.

42. The neurological screening method of claim 22, wherein the cognitive assessment is configured to stress the frontal lobe of the subject.

* * * * *